US012297279B2

(12) United States Patent
Boklage et al.

(10) Patent No.: US 12,297,279 B2
(45) Date of Patent: May 13, 2025

(54) COMPOSITIONS AND METHODS FOR TREATING PAIN IN SUBJECTS WITH RHEUMATOID ARTHRITIS

(71) Applicants: SANOFI BIOTECHNOLOGY, Paris (FR); REGENERON PHARMACEUTICALS, INC., Tarrytown, NY (US)

(72) Inventors: Susan Boklage, Tarrytown, NY (US); Toshio Kimura, Tarrytown, NY (US); Stefano Fiore, Guttenberg, NJ (US); Gregory St John, Tarrytown, NY (US); Wenhui Wei, Tarrytown, NY (US); Vivian Bykerk, New York, NY (US)

(73) Assignees: SANOFI BIOTECHNOLOGY, Gentilly (FR); REGENERON PHARMACEUTICALS, INC., Tarrytown, NY (US)

( * ) Notice: Subject to any disclaimer, the term of this patent is extended or adjusted under 35 U.S.C. 154(b) by 716 days.

(21) Appl. No.: 16/891,984

(22) Filed: Jun. 3, 2020

(65) Prior Publication Data

US 2020/0399380 A1    Dec. 24, 2020

Related U.S. Application Data

(60) Provisional application No. 62/930,966, filed on Nov. 5, 2019, provisional application No. 62/857,247, filed on Jun. 4, 2019.

(30) Foreign Application Priority Data

Feb. 27, 2020 (EP) .................................. 20305191

(51) Int. Cl.
*A61K 39/395* (2006.01)
*A61K 9/00* (2006.01)
*A61P 29/00* (2006.01)
*C07K 16/24* (2006.01)
*C07K 16/28* (2006.01)

(52) U.S. Cl.
CPC ........ *C07K 16/2866* (2013.01); *A61K 9/0019* (2013.01); *A61P 29/00* (2018.01); *C07K 16/241* (2013.01); *C07K 2317/565* (2013.01)

(58) Field of Classification Search
None
See application file for complete search history.

(56) References Cited

U.S. PATENT DOCUMENTS

| 4,997,423 A | 3/1991 | Okuda et al. |
| 5,016,784 A | 5/1991 | Batson |
| 5,215,534 A | 6/1993 | De Harde et al. |
| 5,480,796 A | 1/1996 | Kishimoto |
| 5,605,690 A | 2/1997 | Jacobs et al. |
| 5,670,373 A | 9/1997 | Kishimoto |
| 5,723,120 A | 3/1998 | Brakenhoff et al. |
| 5,795,965 A | 8/1998 | Tsuchiya et al. |
| 5,817,790 A | 10/1998 | Tsuchiya et al. |
| 5,888,510 A | 3/1999 | Kishimoto et al. |
| 5,888,511 A | 3/1999 | Skurkovich et al. |
| 5,908,686 A | 6/1999 | Sudo et al. |
| 6,046,223 A | 4/2000 | Sponsel et al. |
| 6,086,874 A | 7/2000 | Yoshida et al. |
| 6,261,560 B1 | 7/2001 | Tsujinaka et al. |
| 6,286,699 B1 | 9/2001 | Sudo |
| 6,410,691 B1 | 6/2002 | Kishimoto et al. |
| 6,629,949 B1 | 10/2003 | Douglas |
| 6,632,927 B2 | 10/2003 | Adair et al. |
| 6,645,635 B2 | 11/2003 | Murakai |
| 6,659,982 B2 | 12/2003 | Douglas et al. |
| 6,670,373 B1 | 12/2003 | Bonjouklian et al. |
| 6,692,742 B1 | 2/2004 | Nakamura et al. |
| 6,723,319 B1 | 4/2004 | Ito et al. |
| 7,226,554 B2 | 6/2007 | Sudo et al. |
| 7,320,792 B2 | 1/2008 | Ito et al. |
| 7,479,543 B2 | 1/2009 | Tsuchiya et al. |
| 7,521,052 B2 | 4/2009 | Okuda et al. |
| 7,582,298 B2 | 9/2009 | Stevens et al. |
| 8,043,617 B2 | 10/2011 | Stevens et al. |
| 8,080,248 B2* | 12/2011 | Radin .............. A61K 39/39541 424/143.1 |
| 8,183,014 B2 | 5/2012 | Stevens et al. |
| 8,192,741 B2 | 6/2012 | Radin et al. |
| 8,440,890 B1 | 5/2013 | Carlone, Jr. et al. |
| 8,568,721 B2 | 10/2013 | Radin et al. |
| 8,709,409 B2 | 4/2014 | Okuda et al. |

(Continued)

FOREIGN PATENT DOCUMENTS

| BR | PI0712224 A2 | 1/2012 |
| CN | 103476793 A | 12/2013 |

(Continued)

OTHER PUBLICATIONS

Atzeni et al., et al., (2019, Pharmacological research vol. 149, pp. 1-8). (Year: 2019).*
Lamb et al.(2018). Drugs. 78:929-940.*
Huizen et al. 2023). Medical News Today. (4 pages).*
Emery et al. (2007). Rheumatol. Int. 27:793-806.*
U.S. Appl. No. 13/648,521 2013/0149310 U.S. Pat. No. 9,943,594, filed Oct. 10, 2012 Jun. 13, 2013 Apr. 17, 2018, Martine Jasson.

(Continued)

*Primary Examiner* — Christine J Saoud
*Assistant Examiner* — Jon M Lockard
(74) *Attorney, Agent, or Firm* — LATHROP GPM LLP; James H. Velema, Esq.; Judith L. Stone-Hulslander, Esq.

(57) ABSTRACT

The present disclosure relates to the use of an anti-IL6 receptor antibody for treating unacceptable pain in subjects with rheumatoid arthritis. Subjects with unacceptable pain can have, e.g., refractory pain or strict refractory pain.

24 Claims, 3 Drawing Sheets

Specification includes a Sequence Listing.

(56) References Cited

U.S. PATENT DOCUMENTS

| | | |
|---|---|---|
| 8,869,904 B2 | 10/2014 | Jani |
| 8,895,521 B2 | 11/2014 | Klinman et al. |
| 9,139,646 B2 | 9/2015 | Solinger et al. |
| 9,173,880 B2 | 11/2015 | Dix et al. |
| 9,248,242 B2 | 2/2016 | Verespe et al. |
| 9,308,256 B2 | 4/2016 | Radin et al. |
| 9,427,531 B2 | 8/2016 | Hourmand et al. |
| 9,566,395 B2 | 2/2017 | Denny et al. |
| 9,884,916 B2 | 2/2018 | Stevens et al. |
| 9,943,594 B2 | 4/2018 | Jasson et al. |
| 9,951,130 B2 | 4/2018 | Schmidt et al. |
| 10,072,086 B2 * | 9/2018 | Dix .................. A61K 47/26 |
| 10,927,435 B2 | 2/2021 | Huang et al. |
| 10,968,278 B2 | 4/2021 | Sridhara Sundaram et al. |
| 11,498,969 B2 | 11/2022 | Baret-Cormel et al. |
| 2002/0187150 A1 | 12/2002 | Mihara et al. |
| 2003/0092606 A1 | 5/2003 | L'Italien et al. |
| 2003/0113316 A1 | 6/2003 | Kaisheva et al. |
| 2003/0190316 A1 | 10/2003 | Kakuta et al. |
| 2004/0071706 A1 | 4/2004 | Ito et al. |
| 2004/0115197 A1 | 6/2004 | Yoshizaki et al. |
| 2004/0197324 A1 | 10/2004 | Liu et al. |
| 2004/0202658 A1 | 10/2004 | Benyunes |
| 2004/0219156 A1 | 11/2004 | Goldenberg et al. |
| 2005/0142635 A1 | 6/2005 | Tsuchiya et al. |
| 2005/0238644 A1 | 10/2005 | Mihara et al. |
| 2006/0078531 A1 | 4/2006 | Sota |
| 2006/0078532 A1 | 4/2006 | Omoigui |
| 2006/0078533 A1 | 4/2006 | Omoigui |
| 2006/0177436 A1 | 8/2006 | Ghilardi et al. |
| 2006/0251653 A1 | 11/2006 | Okuda et al. |
| 2006/0275294 A1 | 12/2006 | Omoigui |
| 2006/0292147 A1 | 12/2006 | Yoshizaki et al. |
| 2007/0036785 A1 | 2/2007 | Saito et al. |
| 2007/0036788 A1 | 2/2007 | Sheriff et al. |
| 2007/0098714 A1 | 5/2007 | Nishimoto et al. |
| 2007/0143168 A1 | 6/2007 | Stevens et al. |
| 2007/0148169 A1 | 6/2007 | Yoshizaki et al. |
| 2007/0280945 A1 | 12/2007 | Stevens et al. |
| 2008/0124325 A1 | 5/2008 | Ito et al. |
| 2008/0131374 A1 | 6/2008 | Medich et al. |
| 2008/0145367 A1 | 6/2008 | Bove et al. |
| 2008/0269467 A1 | 10/2008 | Allan et al. |
| 2009/0082288 A1 | 3/2009 | Klinman et al. |
| 2010/0316627 A1 | 12/2010 | Stevens et al. |
| 2010/0316636 A1 | 12/2010 | Radin et al. |
| 2011/0098450 A1 | 4/2011 | Igawa et al. |
| 2011/0171241 A1 | 7/2011 | Dix et al. |
| 2011/0245473 A1 | 10/2011 | Igawa et al. |
| 2012/0003697 A1 | 1/2012 | Stevens et al. |
| 2012/0171123 A1 | 7/2012 | Medich et al. |
| 2012/0258098 A1 | 10/2012 | Radin et al. |
| 2013/0014958 A1 | 1/2013 | Jani |
| 2013/0149310 A1 * | 6/2013 | Jasson .................. A61K 31/519 424/139.1 |
| 2014/0255390 A1 | 9/2014 | Radin et al. |
| 2014/0302053 A1 | 10/2014 | Huang et al. |
| 2015/0050277 A1 | 2/2015 | Peters et al. |
| 2016/0002341 A1 | 1/2016 | Dix et al. |
| 2016/0220675 A1 | 8/2016 | Abrahmson |
| 2016/0229916 A1 | 8/2016 | Stevens et al. |
| 2016/0280782 A1 | 9/2016 | Huang et al. |
| 2016/0281106 A1 | 9/2016 | Kim et al. |
| 2017/0166646 A1 | 6/2017 | Sridhara Sundaram et al. |
| 2017/0198045 A1 | 7/2017 | Johnson et al. |
| 2017/0252434 A1 | 9/2017 | Joseph et al. |
| 2017/0360807 A1 | 12/2017 | Zhang et al. |
| 2018/0296670 A1 | 10/2018 | Jasson et al. |
| 2019/0002574 A1 | 1/2019 | Dix et al. |
| 2019/0100585 A1 | 4/2019 | Bauer et al. |
| 2020/0047029 A1 | 3/2020 | Boyapati et al. |
| 2020/0339693 A1 | 10/2020 | Baret-Cormel et al. |
| 2020/0399380 A1 | 12/2020 | Boklage et al. |
| 2020/0405851 A1 | 12/2020 | Boyapati et al. |
| 2021/0230719 A1 | 7/2021 | Huang et al. |
| 2021/0301027 A1 | 9/2021 | Sridhara Sundaram et al. |
| 2021/0240369 A1 | 12/2021 | Feist et al. |
| 2022/0242959 A1 | 8/2022 | Chen et al. |
| 2023/0127528 A1 | 4/2023 | Baret-Cormel et al. |
| 2023/0174657 A1 | 6/2023 | Albrecht et al. |
| 2023/0193871 A1 | 6/2023 | Ford et al. |

FOREIGN PATENT DOCUMENTS

| | | |
|---|---|---|
| CN | 104105505 A | 10/2014 |
| CN | 104903349 A | 9/2015 |
| CN | 102869346 A | 1/2023 |
| EA | 014226 B1 | 10/2010 |
| EA | 014298 B1 | 10/2010 |
| EP | 0628639 A1 | 12/1994 |
| EP | 0409607 B1 | 10/1996 |
| EP | 0783893 A1 | 7/1997 |
| EP | 0800829 A1 | 10/1997 |
| EP | 0811384 A1 | 12/1997 |
| EP | 0923941 A2 | 6/1999 |
| EP | 1004315 A1 | 5/2000 |
| EP | 1074268 A1 | 2/2001 |
| EP | 1108435 A1 | 6/2001 |
| EP | 1314437 A1 | 5/2003 |
| EP | 1327681 A1 | 7/2003 |
| EP | 1475100 A1 | 11/2004 |
| EP | 1475101 A1 | 11/2004 |
| EP | 0413908 B2 | 8/2005 |
| EP | 1810980 A1 | 7/2007 |
| EP | 1334731 B1 | 2/2008 |
| EP | 2451438 B1 | 2/2014 |
| EP | 2766039 A1 | 8/2014 |
| EP | 3071230 A1 | 9/2016 |
| EP | 3193934 A1 | 7/2017 |
| EP | 3371224 A1 | 9/2018 |
| EP | 3426295 A1 | 1/2019 |
| EP | 3770173 A1 | 1/2021 |
| EP | 3983071 A1 | 4/2022 |
| FR | 2694767 A1 | 2/1994 |
| JP | 2009-539349 A | 11/2009 |
| JP | 2014-530226 A | 11/2014 |
| JP | 61-22018 | 4/2017 |
| JP | 61-22018 B2 | 4/2017 |
| JP | 2017-137338 A | 8/2017 |
| JP | 63-36171 B2 | 5/2018 |
| JP | 2020-045351 A | 3/2020 |
| KR | 10-2008-0011665 A | 2/2008 |
| RU | 2358762 C2 | 6/2009 |
| TW | 201141518 A | 12/2011 |
| WO | WO 1992/016553 A1 | 10/1992 |
| WO | WO 1992/019759 A1 | 11/1992 |
| WO | WO 1994/006476 A1 | 3/1994 |
| WO | WO 1995/009873 A1 | 4/1995 |
| WO | WO 1996/011020 A1 | 4/1996 |
| WO | WO 2002/100330 A2 | 12/2002 |
| WO | WO 2003/009817 A2 | 2/2003 |
| WO | WO 2004/039826 A1 | 5/2004 |
| WO | WO 2004/091658 A1 | 10/2004 |
| WO | WO 2004/096273 A1 | 11/2004 |
| WO | WO 2005/028514 A1 | 3/2005 |
| WO | WO 2005/058365 A1 | 6/2005 |
| WO | WO 2005/016280 A2 | 2/2006 |
| WO | WO 2006/033702 A2 | 3/2006 |
| WO | WO 2006/125229 A2 | 11/2006 |
| WO | WO 2007/062040 A1 | 5/2007 |
| WO | WO 2007/070750 A1 | 6/2007 |
| WO | WO 2007/143168 A2 | 12/2007 |
| WO | WO 2007/147001 A2 | 12/2007 |
| WO | WO 2008/020079 A1 | 2/2008 |
| WO | WO 2007/143168 A3 | 4/2008 |
| WO | WO 2008/049897 A1 | 5/2008 |
| WO | WO 2008/145142 A1 | 12/2008 |
| WO | WO 2009/095489 A2 | 8/2009 |
| WO | WO 2009/109584 A1 | 9/2009 |
| WO | WO 2009/125825 A1 | 10/2009 |
| WO | WO 2009/140348 A2 | 11/2009 |
| WO | WO 2010/035769 A1 | 4/2010 |
| WO | WO 2010/106812 A1 | 9/2010 |
| WO | WO 2010/149771 A1 | 12/2010 |

(56) References Cited

FOREIGN PATENT DOCUMENTS

| | | |
|---|---|---|
| WO | WO 2011/085158 A2 | 7/2011 |
| WO | WO 2012/064627 A2 | 5/2012 |
| WO | WO 2013/053751 A1 | 4/2013 |
| WO | WO 2013/056751 A1 | 4/2013 |
| WO | WO 2015/077582 A1 | 5/2015 |
| WO | WO 2015/148790 A1 | 10/2015 |
| WO | WO 2016/044343 A1 | 3/2016 |
| WO | WO 2017/038986 A1 | 3/2017 |
| WO | WO 2017/079443 A1 | 5/2017 |
| WO | WO 2017/106312 A1 | 6/2017 |
| WO | WO 2017/155990 A1 | 9/2017 |
| WO | WO 2017/194779 A1 | 11/2017 |
| WO | WO 2018/007442 A1 | 1/2018 |
| WO | WO 2020/047029 A1 | 3/2020 |
| WO | WO 2020/160465 A1 | 8/2020 |
| WO | WO 2020/219960 A1 | 10/2020 |
| WO | WO 2020/247461 A1 | 12/2020 |
| WO | WO 2020/252214 A1 | 12/2020 |
| WO | WO 2021/240436 A1 | 12/2021 |

OTHER PUBLICATIONS

U.S. Appl. No. 14/350,973 2014/0302053, filed Apr. 10, 2014 Oct. 9, 2014, Xiaohong Huang.

PCT/EP2012/070052 WO 2013/053751, Oct. 10, 2012 Apr. 18, 2013, Xiaohong Huang.

U.S. Appl. No. 15/910,733 20108/0296670, filed Mar. 2, 2018 Oct. 18, 2018, Martine Johnson.

U.S. Appl. No. 15/034,531 2016/0280782, filed May 4, 2016 Sep. 29, 2016, Xiaohong Huang.

PCT/US2014/066856 WO 2015/077582, Nov. 21, 2014 May 28, 2015, Xiaohong Huang.

U.S. Appl. No. 15/505,056 2017/0252434, filed Feb. 17, 2017 Sep. 7, 2017, George Johny Joseph.

PCT/US2015/050291 WO 2016/044343, Sep. 15, 2015 Mar. 24, 2016, George Johny Joseph.

U.S. Appl. No. 15/342,833 2017/0166646, filed Nov. 3, 2016 Jun. 15, 2017, Preethi Aavali Sridhara Sundaram.

PCT/US2016/060344 WO 2017/079443, Nov. 3, 2016 May 11, 2017, Preethi Aavali Sridhara Sundaram.

PCT/US2017/021149 WO 2017/155990, Mar. 7, 2017 Apr. 14, 2017, Deborah Bauer.

U.S. Appl. No. 16/082,841 2019/0100585, filed Sep. 6, 2018 Apr. 4, 2019, Deborah Bauer.

PCT/US2020/016203 WO 2020/160465, Jan. 31, 2020 Aug. 6, 2020, Lydie Baret-Cormel.

U.S. Appl. No. 16/779,187 2020/0339693, filed Jan. 31, 2020 Oct. 29, 2020, Lydie Baret-Cormel.

PCT/US2020/035871 WO 2020/247461, Jun. 3, 2020 Dec. 10, 2020, Susan Boklage.

"Highlights of Prescribing Information" for Kevzara (sarilumab), Reference ID: 4101405—Accessdata.fda.gov, May 2017.

Actemra Prescribing Information Genentech. Actemra (tocilizumab): Full Prescribing Information. 2017 Retrieved from: «https://www.accessdata.fda.gov/drugsatfda_docs/label/2017/125276s114lbl.pdf».

Adlan, et al., Autonomic Function and Rheumatoid Arthritis—A Systematic Review, Seminars in Arthritis and Rheumatism, vol. 44, No. 3, pp. 283-304, 2014.

Alekseeva, "Juvenile Idiopathic Arthritis: Clinical Picture, Diagnosis, Treatment," Current Pediatrics, 2015, 14(1): 78-94, Etiology and Pathogenesis, p. 78; Treatment of Polyarticular (RF-, RF+) Jia, p. 84; and Treatment, p. 92, English Abstract included.

Andersson M. et al., "SAT0116 Prevalence of unacceptable pain in patients with long-standing RA", Annals of the Rheumatic Diseases, 2017, 76: p. 812-813.

Atzeni et al., "Il-6 Involvement in pain, fatigue and mood disorders in rheumatoid arthritis and the effects of Il-6 inhibitor sarilumab", Pharmacological Research, 2019, 149: 1-8.

Biswas, et al., Prevalence, Types, Clinical Associations, and Determinants of Peripheral Neuropathy in Rheumatoid Patients, Annals of Indian Academy of Neurology, vol. 14, No. 3, pp. 194-197, 2011.

Brenn, et al., Sensitization of Unmyelinated Sensory Fibers of the Joint Nerve to Mechanical Stimuli by Interleukin-6 in the Rat: an Inflammatory Mechanism of Joint Pain, Arthritis & Rheumatology, vol. 56, No. 1, pp. 351-359, Jan. 2007.

Burmester et al., "Efficacy and safety of subcutaneous tocilizumab versus intravenous tocilizumab in combination with traditional DMARDs in patients with RA at week 97 (Summacta)", Annals of the Rheumatic Diseases, Jun. 8, 2015, vol. 75, No. 1, pp. 68-74.

Burmester et al., "Rheumatoid Arthritis—Sarilumab more effective than adalimumab", Nature Reviews, Rheumatology, Research Highlights, Published online Dec. 8, 2016.

Burmester et al., "Safety and efficacy of switching from adalimumab to sarilumab in patients with rheumatoid arthritis in the ongoing Monarch open-label extention", RMD Open, Rheumatic and Musculoskeletal Diseases, 2019, 5: e001017.

Burmester, et al. Unique Changes in Hemoglobin with Sarilumab Versus Adalimumab are Independent of Better Disease Control in Patients with Rheumatoid Arthritis (RA) Arthritis & Rheumatology, 2018 vol. 70, Supplement 10, Abstract 1528.

Cazzola et al., Physiopathology of Pain in Rheumatology, Reumatismo, vol. 66, No. 1, pp. 4-13, 2014.

Challa, et al., Patient-provider Discordance Between Global Assessments of Disease Activity in Rheumatoid Arthritis: a Comprehensive Clinical Evaluation, Arthritis Research & Therapy, vol. 19, No. 212, pp. 1-14, 2017.

ClinicalTrials.gov, (Feb. 26, 2015) "A Study Assessing the Safety and Efficacy of Sarilumab Added to Non-MTX DMARDs or as Monotherapy in Japanese Patients With Active Rheumatoid Arthritis", ClinicalTrials.gov Identifier: NCT02373202.

ClinicalTrials.gov, (Jun. 8, 2015) "Phase II Study to Analyze Sarilumab in Non-Infectious Uveitis", ClinicalTrials.gov Identifier: NCT01900431.

ClinicalTrials.gov, (Oct. 7, 2010), "Evaluation of Sarilumab (SAR153191/REGN88) on Top of Methotrexate in Rheumatoid Arthritis Patients (RA-Mobility)", ClinicalTrials.gov Identifier: NCT01061736.

Curtis, et al. Reanalysis of the Multi-Biomarker Disease Activity Score for Assessing Disease Activity in the Abatacept Versus Adalimumab Comparison in Biologic-Naive Rheumatoid Arthritis Subjects with Background Methotrexate Study: Comment on the Article by Fleischmann, Arthritis & Rheumatology, Apr. 2017, vol. 69, No. 4, pp. 863-872.

Dasgupta et al., "Sarilumab in Patients With Relapsing Polymyalgia Rheumatica: A Phase 3, Multicenter, Randomized, Double Blind, Placebo Controlled Trial (Saphyr)", Annals of The Rheumatic Diseases, Eular European Congress of Rheumatology (Eular); Copenhagen, Denmark; Jun. 1-4, 2022, British Medical Association, GB, May 31, 2022, 81(Suppl. 1): 210-211.

De Haas, et al., Rheumatoid Arthritis, Typus Robustus, Annals of the Rheumatic Diseases, vol. 32, No. 1, pp. 91-92, 1973.

Deane, et al., Preclinical Rheumatoid Arthritis: Identification, Evaluation, and Future Directions for Investigation, Rheumatic Disease Clinics of North America, vol. 36, No. 2, pp. 213-241, 2010.

Durán, et al., The Effect on Treatment Response of Fibromyalgic Symptoms in Early Rheumatoid Arthritis Patients: Results From the Espoir Cohort, Rheumatology, vol. 54, No. 12, pp. 2166-2170, 2015.

Eberhard A., et al., "AB0285 Predictors of unacceptable pain and unacceptable pain with low inflammation, in early rheumatoid arthritis", Annals of the Rheumatic Diseases, pp. 1600, 2019.

Flodin, et al., Intrinsic Brain Connectivity in Chronic Pain: A Resting-State fMRI Study in Patients with Rheumatoid Arthritis, Frontiers in Human Neuroscience, vol. 10, No. 107, pp. 1-8, Mar. 2016.

Genentech (Apr. 11, 2019) Actemra® (tocilizumab) injection, for intravenous or subcutaneous use.

Hammer, et al., Major Reduction of Ultrasound Detected Synovitis during Subcutaneous Tocilizumab Treatment; Results from a Multicenter 24 Weeks Study of Patients with Rheumatoid Arthritis, Arthritis & Rheumatology, vol. 70, No. S9, pp. 1537-1538, 2018.

(56) References Cited

OTHER PUBLICATIONS

Hashimoto et al., "Increase of Hemoglobin Levels by Anti-IL-6 Receptor Antibody (Tocilizumab) in Rheumatoid Arthritis", PLoS One, May 30, 2014, vol. 9, No. 5, pp. e98202: 1-7.

International Search Report with Written Opinion corresponding to International Patent Application No. PCT/US2023/065361, mailed Jul. 14, 2023.

Khan, et al., Determinants of Discordance in Patients' and Physicians' Rating of Rheumatoid Arthritis Disease Activity, Arthritis Care & Research (Hoboken), vol. 64, No. 2, pp. 206-214, 2012.

Kimel et al., "Adalimumab plus methotrexate improved SF-36 scores and reduced the effect of rheumatoid arthritis (RA) on work activity for patients with early RA", The Journal of Rheumatology, Feb. 2008, 35(2): 206-215.

Klein, et al. FRI0549—Efficacy and Safety of Tocilizumab in Systemic and Polyarticular Juvenile Idiopathic Arthritis—Data of Toe Biker Registry Squibb, Johnson & Johnson, Novartis, Pfizer, Fieckitt Benkiser, and Roche Jun. 14, 2019 pp. 969-970.

Kristensen, et al., Is Swollen to Tender Joint Count Ratio a New and Useful Clinical Marker for Biologic Drug Response in Rheumatoid Arthritis? Results From a Swedish Cohort, Arthritis Care & Research (Hoboken), vol. 66, No. 2, pp. 173-179, 2014.

Lamb et al., "Sarilumab: A Review in Moderate to Severe Rheumatoid Arthritis Drugs", Drugs, 2018, 78: 929-940.

Lee, et al., Pain Persists in DAS28 Rheumatoid Arthritis Remission but Not in ACR/EULAR Remission: a Longitudinal Observational Study, Arthritis Research & Therapy, vol. 13, No. R83, pp. 1-9, 2011.

Maini, et al., Infliximab (Chimeric Anti-Tumour Necrosis Factor A Monoclonal Antibody) Versus Placebo in Rheumatoid Arthritis Patients Receiving Concomitant Methotrexate: a Randomised Phase III Trial, The Lancet, vol. 354, No. 9194, pp. 1932-1939, 1999.

McWilliams, et al., Pain Mechanisms in Rheumatoid Arthritis, Clinical and Experimental Rheumatology, vol. 35, No. 5, pp. S94-S101, 2017.

Montaño et al., "Influence of the Isotype of the Light Chain on the Properties of IgG", Journal of Immunology, 2002, 168: 224-231.

Nasonov, E.L. et al., "Prospects of pharmacotherapy rheumatoid arthritis: monoclonal antibodies", Nauchnopraktych Rheumatol., 2012, 52(3): 75-82.

New Drug Approvals Retrieved from: «https://www.drugs.com/newdrugs.html» pp. 1-7, 2019.

Nieminen, et al., "The Use of the ATF System to Culture Chinese Hamster Ovary Cells in a Concentrated Fed-Batch System", BioPharm International, vol. 24, Issue 6, pp. 1-8, Jun. 1, 2011.

Non-Final Office Action received for U.S. Appl. No. 13/648,521, mailed on Jul. 3, 2014.

Non-Final Office Action received for U.S. Appl. No. 13/648,521, mailed on Jun. 26, 2015.

Non-Final Office Action received for U.S. Appl. No. 13/648,521, mailed on Mar. 19, 2015.

Non-Final Office Action received for U.S. Appl. No. 13/648,521, mailed on Oct. 18, 2013.

Non-Final Office Action received for U.S. Appl. No. 14/350,973, mailed on Feb. 5, 2016.

Non-Final Office Action received for U.S. Appl. No. 14/350,973, mailed on Oct. 18, 2019.

Notice of Allowance received for U.S. Appl. No. 14/350,973, mailed on Jun. 14, 2016.

Ogata et al., "Phase III Study of the Efficacy and Safety of Subcutaneous Versus Intravenous Tocilizumab Monotherapy in Patients With Rheumatoid Arthritis", Arthritis Care & Research, Aug. 27, 2013, vol. 66, No. 3, pp. 344-354.

Patel et al., "The Negative Effect of Carpal Tunnel Syndrome on Sleep Quality", Sleep Disorders, Feb. 17, 2014, Article ID 962746.

Paul et al., "Effectiveness of biologic and non-biologic antirheumatic drugs on anaemia markers in 153,788 patients with rheumatoid arthritis: New evidence from real-world data", Seminars in Arthritis and Rheumatism, Feb. 1, 2018, vol. 47, No. 4, pp. 478-484.

Pelechas et al., "Clinical evaluation of the safety, efficacy and tolerability of sarilumab in the treatment of moderate to severe rheumatoid arthritis", Therapeutics and Clinical Risk Management, Sep. 1, 2019, vol. 15, pp. 1073-1079.

Pollard, et al., Fibromyalgic Rheumatoid Arthritis and Disease Assessment, Rheumatology, vol. 49, No. 5, pp. 924-928, Jan. 25, 2010.

Pulawski et al., "Certain therapies linked to pulmonary toxicity among patients with rheumatic diseases", Healio, May 20, 2015, obtained from url: https://www.healio.com/news/rheumatology/20150520/certain-therapies-linked-to-pulmonary-toxicity-among-patients-with-rheumatic-diseases.

Sarzi-Puttini, et al., Correlation of the Score for Subjective Pain With Physical Disability, Clinical and Radiographic Scores in Recent Onset Rheumatoid Arthritis, BMC Musculoskeletal Disorders, vol. 3, No. 18, pp. 1-4, Jul. 19, 2002.

Schaible, Nociceptive Neurons Detect Cytokines in Arthritis, Arthritis Research & Therapy, vol. 16, No. 470, pp. 1-9, 2014.

Scott, "Sarilumab: First Global Approval", Drugs, 2017, 77: 705-712.

Seth, et al., "Development of a New Bioprocess Scheme Using Frozen Seed Train Intermediates to Initiate CHO Cell Culture Manufacturing Campaigns", Biotechnology and Bioengineering, May 2013, vol. 110, Issue 5, pp. 1376-1385.

Spectrum Laboratories, Inc., "Hollow Fiber Filters", Datasheet [online], Spectrumlabs.com, Copyright 1995-2015, Retrieved from: »URL: http://www.spectrumlabs.com/filtration/mPESKrosFloList.html», Retrieved on: Jun. 12, 2015.

Steel et al., "2015 Eular-ACR recommendations for polymyalgia rheumatica: the message and next steps", Rheumatology, Jun. 17, 2016, 55(6): 955-956, Advance Access Publication Dec. 17, 2015.

Strand et al., "Sustained benefit in rheumatoid arthritis following one course of rituximab: improvements in physical function over 2 years", Rheumatology, 2006, 45(12): 1505-1513.

Strand, et al., Sarilumab Improves Patient-reported Outcomes in Rheumatoid Arthritis Patients With Inadequate Response/Intolerance to Tumour Necrosis Factor Inhibitors, RMD Open, vol. 3, e000416, 2017.

Strand, et al., Sarilumab Plus Methotrexate Improves Patient-reported Outcomes in Patients With Active Rheumatoid Arthritis and Inadequate Responses to Methotrexate: Results of a Phase III Trial, Arthritis Research & Therapy, vol. 18, No. 198, pp. 1-10, 2016.

Studenic, et al., Discrepancies Between Patients and Physicians in Their Perceptions of Rheumatoid Arthritis Disease Activity, Arthritis & Rheumatology, vol. 64, No. 9, pp. 2814-2823, 2012.

Taylor, et al., Patient Perceptions Concerning Pain Management in the Treatment of Rheumatoid Arthritis, The Journal of International Medical Research, vol. 38, No. 4, pp. 1213-1224, 2010.

Turnier et al., "Tocilizumab for treating juvenile idiopathic arthritis", Expert Opinion on Biological Therapy, 2016, 16(4): 559-566.

Ueno et al., "3-145: The efficacy and safety of additional tocilizumab in patients with polymyalgia rheumatica resistant to or intolerant of conventional therapy", AU, Apr. 1, 2019, 22(S3): 204.

Walsh, et al., Mechanisms, Impact and Management of Pain in Rheumatoid Arthritis, Nature Reviews Rheumatology, vol. 10, No. 10, pp. 581-592, 2014.

Wolfe et al., "Sleep Disturbance in Patients with Rheumatoid Arthritis: Evaluation by Medical Outcomes Study and Visual Analog Sleep Scales", J Rheumatol., 2006, 33:1942-1951.

Woods, et al., "Container System for Enabling Commercial Production of Cryopreserved Cell Therapy Products", Regenerative Medicine, vol. 5, No. 4, pp. 659-667, Jul. 15, 2010.

Yamamura, "FRI0266. The Real-World Efficacy of the 2015 Eular/ACR Recommendations for the Management of Polymyalgia Rheumatica with Additional Tocilizumab Therapy", Annals of the Rheumatic Diseases, Jun. 13, 2020, 79(Suppl 1), 717.2-718.

Yang, et al., Chronic Pain: Structural and Functional Changes in Brain Structures and Associated Negative Affective States, International Journal of Molecular Sciences, vol. 20, No. 13, p. 3130, Jun. 26, 2019.

(56) References Cited

OTHER PUBLICATIONS

Yoo et al., "Exosomal amyloid A and lymphatic vessel endothelial hyaluronic acid receptor-1 proteins are associated with disease activity in rheumatoid arthritis", Arthritis Research & Therapy, 2017, 19(1): 119.
Yoshii, I. et al., "Influence of pain score measured by a visual analog scale (PS-VAS) on the Health Assessment Questionnaire Disability Index and 28 joint- Disease Activity Index with C-reactive protein in rheumatoid arthritis patients", Int J, Rheum Did, 2018, 21: 1955-1961.
Zhou, et al., Interleukin-6: An Emerging Regulator of Pathological Pain, Journal of Neuroinflammation, vol. 13, No. 141, pp. 1-9, 2016.S.
Boyapati, et al., "Sarilumab Plus Methotrexate Suppresses Circulating Biomarkers of Bone Resorption and Synovial Damage in Patients with Rheumatoid Arthritis and Inadequate Response to Methotrexate: A Biomarker Study of Mobility", Arthritis Research & Therapy, vol. 18, Article No. 225, pp. 1-12, Dec. 1, 2016.
Boyden et al., Non-inflammatory Causes of Pain in Patients with Rheumatoid Arthritis, Curr Rheumatol Rep., 2016, 18: 30.1.
Calabrese, et al., "IL-6 Biology: Implications for Clinical Targeting in Rheumatic Disease", Nature Reviews Rheumatology, vol. 10, No. 12, pp. 720-727, Dec. 2014.
Center for Drug Evaluation and Research, Application No. 761037 (Year: 2016).
Cheung, et al., "2-093 Comparative Effectiveness of Biologic Dmards and Jak Inhibitors in Patients With an Inadequate Response to TNF Inhibitors: a Network Meta-analysis", International Journal of Rheumatic Diseases, Retrieved From url: «https://onlinelibrary.wiley.com/doi/10.1111/1756-185X.13545». (2019).
Choy et al., "Indirect Treatment Comparison of the Efficacy and Safety of Sarilumab Monotherapy in Rheumatoid Arthritis Patients with Inadequate Response to Conventional Disease-Modifying Antirheumatic Drugs", Mar. 12, 2019, 36(4): 817-827.
Choy, "Understanding the Dynamics: Pathways Involved in the Pathogenesis of Rheumatoid Arthritis", Rheumatology, vol. 51, Supplement 5, pp. v3-v11, Jul. 1, 2012.
Choy, et al., "Cardiovascular Risk in Rheumatoid Arthritis: Recent Advances in the Understanding of the Pivotal Role of Inflammation", Risk Predictors and the Impact of Treatment Rheumatology, vol. 53, pp. 2143-2154, Dec. 1, 2014.
Choy, et al., "Neuroendocrine and Neurophysiological Effects of Interleukin 6 in Rheumatoid Arthritis", Rheumatology, vol. 57, pp. 1885-1895, Nov. 1, 2018.
ClinicalTrials.gov (Oct. 22, 2019) "Efficacy and Safety of GSK3196165 (Otilimab) Versus Placebo and Sarilumab in Participants With Moderately to Severely Active Rheumatoid Arthritis Who Have an Inadequate Response to Biological Disease-modifying Antirheumatic Drug (DMARDs) and/or Janus Kinase (JAK) Inhibitors (contRAst 3)", ClinicalTrials.gov Identifier: NCT04134728, Retrieved From url: «https://clinicaltrials.gov/ct2/show/NCT04134728».
clinicaltrials.gov, "A Repeated Dose-finding Study of Sarilumab in Children and Adolescents With Systemic Juvenile Idiopathic Arthritis (SKYPS)", ClinicalTrials.gov Identifier: NCT02991469, Dec. 13, 2016.
Clinicaltrials.gov, "An Open-label, Ascending, Repeated Dose-finding Study of Sarilumab in Children and Adolescents With Polyarticular-course Juvenile Idiopathic Arthritis (pcJIA) (SKYPP)", ClinicalTrials.gov Identifier: NCT02776735, May 18, 2016.
ClinicalTrials.gov. (Feb. 2, 2010) "Evaluation of SARI 53191(REGN88) (Sarilumab) on Top of Methotrexate in Rheumatoid Arthritis Patients (RA-Mobility)," ClinicalTrials.gov. http://clinicaltrials.gov/show/NCT01061736.
ClinicalTrials.gov. (Nov. 7, 2013) "Evaluation of SARI 53191(REGN88) (Sarilumab) on Top of Methotrexate in Rheumatoid Arthritis Patients (RA-Mobility)," View of NCT01061736 on Nov. 7, 2013, ClinicalTrials.gov. Accessible on the Internet at URL: https://clinicaltrials.gov/archive/NCT01061736/2013_11_07.

ClinicalTrials.gov. (Oct. 7, 2010) "Effect of SARI 53191 (REGN88) With Methotrexate in Patients With Active Rheumatoid Arthritis Who Failed INF-a Blockers," ClinicalTrials.gov., http://clinicaltrials.gov/show/NCT01217814.
ClinicalTrials.gov. (Sep. 27, 2011) "Effect of SARI 53191 (REGN88) With Methotrexate in Patients With Active Rheumatoid Arthritis Who Failed INF-a Blockers," View of NCT01217814 on Sep. 27, 2011, ClinicalTrials.gov. Accessible on the Internet at JRL: https://clinicaltrials.gov/archive/NCT01217814/2011_09_27.
Corevitas, Rheumatoid Arthritis Registry, Available from: https://www.corevitas.com/registry/rheumatoid-arthritis, Accessed on Aug. 26, 2022.
Cronstein, "Low-Dose Methotrexate: A Mainstay in the Treatment of Rheumatoid Arthritis", Pharmacological Reviews, Jun. 2005, 57(2): 163-172.
Curtis et al., "Determining the minimally important difference in the clinical disease activity index for improvement and worsening in early rheumatoid arthritis patients", Arthritis Care Res (Hoboken), 2015, 67(10): 1345-1353.
De Benedetti et al., "FRI0549—Sarilumab, a Human Monoclonal Antibody to the Interleukin-6 (IL-6) Receptor, In Polyarticular-Course Juvenile Idiopathic Arthritis (pcJIA): A 12-Week Multinational Open-Label Dose-Finding Study", Annals of the Rheumatic Diseases, Jun. 2019, 78(Suppl 2): 969-970.
De Benedetti et al., "Sarilumab, a Human Monoclonal Antibody to the Interleukin-6 Receptor, in Polyarticular-course Juvenile Idiopathic Arthritis: A 12-week, Multinational, Open-label, Dose-Finding Study", Meeting: 2019 ACR/ARP Annual Meeting, American College of Rheumatology, Abstract No. 2710, Nov. 12, 2019.
Dennis Jr., et al., "Synovial Phenotypes in Rheumatoid Arthritis Correlate with Response to Biologic Therapeutics", Arthritis Research & Therapy, vol. 16, Article No. R90, pp. 1-18, Apr. 2014.
Dhillon, Intravenous Tocilizumab: A Review of Its Use in Adults with Rheumatoid Arthritis, BioDrugs, vol. 28, pp. 75-106, 2014.
Elixhauser, et al., Comorbidity Measures for Use with Administrative Data, Medical Care, vol. 36, No. 1, pp. 8-27, Jan. 1988.
Extended European Search Report received for European Patent Application No. 20167644.2, mailed on Oct. 21, 2020, 8 Pages.
Feist, et al., "Abstract 0832 Prosara—A Prospective, Multicenter, Noninterventional Study to Evaluate the Safety and Effectiveness of Sarilumab for the Treatment of Active Rheumatoid Arthritis in Regular Care in Germany", ACR Convergence, Nov. 5-9, 2020, Meeting Abstracts.
Feist, et al., "THU0165 Prosara—a Prospective, Multicenter, Noninterventional Study to Evaluate the Safety and Effectiveness of Sarilumab for the Treatment of Active Rheumatoid Arthritis in Regular Care in Germany", Annals of the Rheumaic Diseases, Scientific Abstracts, Jun. 2020.
Fleischmann et al., "Efficacy and Safety of Sarilumab in Connection with CsDMARDs in Patients with Active Rheumatoid Arthritis Who Were Inadequate Responders or Intolerant of Anti-TNF-alpha Therapy: Results from a Phase 3 Study", ACR Abstract 970; Nov. 8, 2015.
Fleischmann, et al., "Estimating Disease Activity using Multi-Biomarker Disease Activity Scores in Rheumatoid Arthritis Patients Treated with Abatacept or Adalimumab", Arthritis & Rheumatology, vol. 68, No. 9, pp. 2083-2089, Sep. 2016.
Fleischmann, et al., "Sarilumab and Nonbiologic Disease-Modifying Antirheumatic Drugs in Patients with Active Rheumatoid Arthritis and Inadequate Response or Intolerance to Tumor Necrosis Factor Inhibitors", Arthritis & Rheumatology, vol. 69, No. 2, pp. 277-290, Feb. 2017.
Fortin, et al., "Glossary of Selected Terms—A Systematic Review of Intravitreal Bevacizumab for the Treatment of Diabetic Macular Edema" NCBI Bookshelf, XP055753991, Retrieved from: «https://www.ncbi.nlm.nih.gov/books/NBK169468/», 2 Pages, May 1, 2012.
Fragiadaki et al., Sleep Disturbances and Interleukin 6 Receptor Inhibition in Rheumatoid Arthritis, J Rheumatol., 2012, 39: 60-62.
Gabay et al., "Tocilizumab monotherapy versus adalimumab monotherapy for treatment of rheumatoid arthritis (Adacta): a randomised, double-blind, controlled phase 4 trial", Lancet, 2013, 381(9877): 1541-1550.

(56) References Cited

OTHER PUBLICATIONS

Gabay, et al., "Comparison of Lipid and Lipid-Associated Cardiovascular Risk Marker Changes After Treatment With Tocilizumab or Adalimumab in Patients with Rheumatoid Arthritis", Annals of the Rheumatic Diseases, vol. 75, pp. 1806-1812, Oct. 1, 2016.
Gabay, et al., "Effect of Sarilumab on Circulating Biomarkers of Bone and Joint Destruction in Patients with Rheumatoid Arthritis with Inadequate Response to Methotrexate", Arthritis & Rheumatology, vol. 68, Supplement 10, p. 3091, Oct. 2016.
Gabay, et al., "Identification of Sarilumab Pharmacodynamic and Predictive Markers in Patients with Inadequate Response to TNF Inhibition: A Biomarker Substudy of the Phase 3 Target Study", Rheumatic & Musculoskeletal Diseases Open, vol. 4, e000607, pp. 1-11, Mar. 1, 2018.
Garces, et al., Comparison of Dose Escalation and Costs of Dose Escalation Between Patients With Rheumatoid Arthritis Initiating Biologic Treatment With Etanercept, Adalimumab, or Infliximab, Value in Health, vol. 19, No. 3, pp. A229-A230, 2016.
Gavrilă, et al., "Biomarkers in Rheumatoid Arthritis, What is New?", Journal of Medicine and Life, vol. 9, Issue 2, pp. 144-148, Apr.-Jun. 2016.
Genbank, "*H. sapiens* Serum Amyloid A Protein mRNA", Complete cds, Genbank Accession No. M81349.1, Retrieved from: «https://www.ncbi.nlm.nih.gov/nuccore/M81349.1», 1 Page, (1992).
Genbank, "*Homo sapiens* C-Reactive Protein (CRP)", RefSeqGene on Chromosome 1, Genbank Accession No. NG_013007.1, Retrieved from: «https://www.ncbi.nlm.nih.gov/nuccore/NG_013007.1», pp. 1-4, (2018).
Genbank, "*Homo sapiens* C-X-C Motif Chemokine Ligand 13 (CXCL13)", Transcript Variant 1, mRNA, Genbank Accession No. NM_006419.2, Retrieved from: «https://www.ncbi.nlm.nih.gov/nuccore/NM_006419.2», pp. 1-4., Jul. 31, 2008.
Genbank, "*Homo sapiens* Intercellular Adhesion Molecule 1 (ICAM1)", mRNA, Genbank Accession No. NM_000201.3, Retrieved from: «https://www.ncbi.nlm.nih.gov/nuccore/NM_000201.3», pp. 1-5., Nov. 23, 2018.
Genbank, *Homo sapiens* Matrix Metallopeptidase 3 (MMP3), mRNA, Genbank Accession No. NM_002422.5, Retrieved from: «https://www.ncbi.nlm.nih.gov/nuccore/NM_002422.5», pp. 1-4, Nov. 22, 2018.
Genovese, et al., "293 A Phase 3 Clinical Program of Three, Randomized, Double-blind, Placebo- and Comparator-controlled Studies to Assess the Efficacy and Safety of Otilimab in RA: Study Design and Methodology", Journal of Clinical Rheumatology, Retrieved From url:«https://journals.lww.com/jclinrheum/Fulltext/2020/04001/22nd_PANLAR_Congress_Miami,_FL,_August_12_15_2020.1.aspx».
Genovese, et al., "Efficacy and Safety of Sarilumab in Combination With csDMARDs or as Monotherapy in Subpopulations of Patients With Moderately to Severely Active Rheumatoid Arthritis in Three Phase III Randomized", Controlled Studies, Arthritis Research & Therapy, vol. 22, No. 1, pp. 1-17, 2020.
Genovese, et al., "Long-term Safety and Efficacy of Sarilumab Plus Methotrexate on Disease Activity, Physical Function and Radiographic Progression: 5 Years of Sarilumab Plus Methotrexate Treatment", Rheumatic & Musculoskeletal Disease, vol. 5, No. 2, pp. 1-10, 2019.
Genovese, et al., "Switching Between the JAK1-selective Inhibitor Upadacitinib and Adalimumab Following Initial Non-response: Clinical and Functional Outcomes Among Rheumatoid Arthritis Patients", Oral Presentations, Jun. 12, 2019, RA therapy—JAK inhibitors and beyond.
Genovese, et al., Interleukin-6 Receptor Inhibition With Tocilizumab Reduces Disease Activity in Rheumatoid Arthritis With Inadequate Response to Disease-modifying Antirheumatic Drugs: the Tocilizumab in Combination With Traditional Disease-modifying Antirheumatic Drug Ther, Arthritis & Rheumatism: Official Journal of the American College of Rheumatology, vol. 58, No. 10, pp. 2968-2980, Sep. 29, 2008.

Georgy, et al., A Clinical Study to Assess the Pharmacokinetics and Pharmacodynamics of Tocilizumab After a Single Dose Administration by Subcutaneous and Intra Venous Routes to Healthy Subjects, Clinical Pharmacology & Therapeutics, vol. 87, No. S1, p. S60, Feb. 15, 2010.
Heidari et al., "Rheumatoid Arthritis: Early Diagnosis and Outcomes", Caspian Journ Intern Med., Winter 2011, 2(1): 161-170.
Humira® (Adalimumab) Injection, for Subcutaneous Use, Highlights of Prescribing Information, United States Food and Drug Administration, Retrieved from: «https://www.accessdata.fda.gov/drugsatfda_docs/label/2018/125057s410lbl.pdf», 104 Pages, Dec. 2018.
Hunter, et al., "IL-6 as a Keystone Cytokine in Health and Disease", Nature Immunology, vol. 16, No. 5, pp. 448-457, May 2015.
Imagawa et al., "Safety and efficacy of tocilizumab, an anti-IL-6-receptor monoclonal antibody, in patients with polyarticular-course juvenile idiopathic arthritis", Modern Rheumatology, Jun. 12, 2011, 22(1): 109-115.
International Search Report and Written Opinion for PCT International Patent Application No. PCT/US2020/016203, mailed Jul. 14, 2020.
International Search Report and Written Opinion received for PCT Patent Application No. PCT/US2017/021149, mailed on Jul. 18, 2017.
International Search Report and Written Opinion Received for PCT Application No. PCT/US2020/037325, mailed on Oct. 27, 2020.
International Search Report and Written Opinion received for PCT Patent Application No. PCT/US2016/060344, mailed on Mar. 13, 2017.
International Search Report and Written Opinion received for PCT Patent Application No. PCT/US2020/029930, mailed on Oct. 8, 2020.
International Search Report and Written Opinion received for PCT Patent Application No. PCT/IB2021/054652, mailed on Aug. 30, 2021.
International Search Report and Written Opinion received for PCT Patent Application No. PCT/IB2021/054546, mailed on Sep. 14, 2021.
International Search Report with Written Opinion corresponding to International Patent Application No. PCT/EP2012/070052, mailed Dec. 7, 2012.
International Search Report with Written Opinion corresponding to International Patent Application No. PCT/US2014/066856, mailed Apr. 2, 2015.
International Search Report with Written Opinion corresponding to International Patent Application No. PCT/US2015/050291, mailed Dec. 1, 2015.
Jones, et al., Comparison of Tocilizumab Monotherapy Versus Methotrexate Monotherapy in Patients With Moderate to Severe Rheumatoid Arthritis: the Ambition Study, Annals of the Rheumatic Diseases, vol. 69, No. 01, pp. 88-96, 2010.
Kaneko, Tocilizumab in Rheumatoid Arthritis: Efficacy, Safety and Its Place in Therapy, Therapeutic Advances in Chronic Disease, vol. 4, No. 1, pp. 15-21, 2013.
Karmakar, et al., "Bone Damage in Rheumatoid Arthritis—Mechanistic Insights and Approaches to Prevention", Rheumatic Diseases Clinics of North America, vol. 36, No. 2, 19 Pages, May 1, 2010.
Kojima, et al., Depression, Inflammation, and Pain in Patients With Rheumatoid Arthritis, Arthritis & Rheumatism (Arthritis Care & Research), vol. 61, No. 8, pp. 1018-1024, Aug. 15, 2009.
Kremer, et al., Tocilizumab Inhibits Structural Joint Damage in Rheumatoid Arthritis Patients With Inadequate Responses to Methotrexate, Arthritis & Rheumatism vol. 63, No. 3, pp. 609-621, 2011.
Kringelbach, et al., "Identification of New Biomarkers to Promote Personalised Treatment of Patients with Inflammatory Rheumatic Disease: Protocol for an Open Cohort Study", British Medical Journal Open, vol. 8, e019325, pp. 1-8., Feb. 1, 2018.
Lee et al., "Disease modifying drugs in adult rheumatoid arthritis", Australian Prescriber, Apr. 2003, 26: 36-40.
Lipsky, "Interleukin-6 and Rheumatic Diseases", Arthritis Research & Therapy, vol. 8, Suppl 2, S4, pp. 1-5, Jan. 1, 2006.

(56) References Cited

OTHER PUBLICATIONS

Maini, et al., Double-blind Randomized Controlled Clinical Trial of the Interleukin-6 Receptor Antagonist, Tocilizumab, in European Patients With Rheumatoid Arthritis Who Had an Incomplete Response to Methotrexate, Arthritis & Rheumatism, vol. 54, No. 9, pp. 2817-2829, Aug. 31, 2006.

Matcham, et al., Psychological Correlates of Fatigue in Rheumatoid Arthritis: A Systematic Review, Clinical Psychology Review, vol. 39, pp. 16-29, Jul. 2015.

Matcham, et al., Symptoms of Depression and Anxiety Predict Treatment Response and Long-term Physical Health Outcomes in Rheumatoid Arthritis: Secondary Analysis of a Randomized Controlled Trial, Rheumatology, vol. 55, Issue 2, pp. 268-278, Feb. 2016.

Matcham, et al., The Prevalence of Depression in Rheumatoid Arthritis: A Systematic Review and Meta-analysis, Rheumatology, vol. 52, Issue 12, pp. 2136-2148, Sep. 3, 2013.

Matteson, "Current Treatment Strategies for Rheumatoid Arthritis", Mayo Clinic Proceedings, vol. 75, pp. 69-74, Jan. 2000.

McInnes, et al., "Cytokines in the Pathogenesis of Rheumatoid Arthritis", Nature Reviews, Immunology, vol. 7, pp. 429-442, Jun. 2007.

Medscape, Actemra, Retrieved online: <URL: https://reference.medscape.com/drug/actennra-tocilizunnab-999419>, Retrieved on Feb. 8, 2022.

Millar et al., Inflammatory mechanisms in tendinopathy—towards translation, Nature, Feb. 2017, 13: 110-122.

Nadkarni, et al., Incidence of Dose Escalation and Impact on Biologic Costs Among Patients With Rheumatoid Arthritis Treated With Three Intravenous Agents, Journal of Comparative Effectiveness Research, vol. 6, No. 8, pp. 671-682, 2017.

NCBI, C-Reactive Protein Isoform 1 Precursor [*Homo sapiens*], NCBI Reference Sequence: NP_001315986.1, Retrieved from: «https://www.ncbi.nlm.nih.gov/protein/NP_001315986.1», pp. 1-3, Jun. 29, 2016.

NCBI, C-X-C Motif Chemokine 13 Precursor [*Homo sapiens*], NCBI Reference Sequence: NP_006410.1, Retrieved from: «https://www.ncbi.nlm.nih.gov/protein/NP_006410.1», pp. 1-3, (2024).

NCBI, Intercellular Adhesion Molecule 1 Precursor [*Homo sapiens*], NCBI Reference Sequence: NP_000192.2, Retrieved from: «https://www.ncbi.nlm.nih.gov/protein/NP_000192.2», pp. 1-4, Feb. 8, 2008.

NCBI, Matrix Metallopeptidase 3 (Stromelysin 1, Progelatinase) [*Homo sapiens*], NCBI Reference Sequence: EAW67032.1, Retrieved from: «https://www.ncbi.nlm.nih.gov/protein/EAW67032.1», pp. 1-2, (2005).

NCBI, Serum Amyloid A [*Homo sapiens*], NCBI Reference Sequence: AAB24060.1, Retrieved from: «https://www.ncbi.nlm.nih.gov/protein/AAB24060.1», 1 Page. (1992).

Nihon Naika Gakkai Zasshi, Japan Internal Medical Association Magazine, vol. 101, No. 10, pp. 2893-2898, (2012).

Nishimoto, et al., Humanized Antihuman IL-6 Receptor Antibody, Tocilizumab, Part of the Handbook of Experimental Pharmacology, vol. 181, Therapeutic Antibodies, pp. 151-160, 2008.

Ogata, et al., Long-term Safety and Efficacy of Weekly Subcutaneous Tocilizumab Monotherapy in Patients With Rheumatoid Arthritis Who Had an Inadequate Response to Subcutaneous Tocilizumab Every Other Week: Results From the Open-label Extension of the Shinobi Study, Modern Rheumatology, vol. 29, Issue 5, pp. 767-774, Sep. 3, 2019.

Ogata, et al., Subcutaneous Tocilizumab: Recent Advances for the Treatment of Rheumatoid Arthritis, Expert Opinion on Drug Delivery, vol. 16, Issue 6, pp. 639-648, Jun. 3, 2019.

Ohta, et al., Optimal Dose Prediction by Pharmacokinetic and Biomarker Response of Subcutaneous Tocilizumab Treatment A Phase I/II Study Evaluating the Safety, Pharmacokinetics and Clinical Response in Patients with Rheumatoid Arthritis, Arthritis & Rheumatism, vol. 62, Supplement 10, pp. 1-2, Oct. 1, 2010.

Overman, et al., The Prospective Association Between Psychological Distress and Disease Activity in Rheumatoid Arthritis: a Multilevel Regression Analysis, Annals of the Rheumatic Diseases, vol. 71, No. 2, pp. 192-197, 2012.

Pappas, et al., Dosing of Intravenous Tocilizumab in a Real-World Setting of Rheumatoid Arthritis: Analyses from the Corrona Registry, Rheumatology and Therapy, vol. 3, pp. 103-115, Feb. 8, 2016.

Pincus, Limitations of a Quantitative Swollen and Tender Joint Count to Assess and Monitor Patients with Rheumatoid Arthritis, Bulletin of the NYU Hospital for Joint Diseases, 2008, 66(3): 216-223.

Redlich et al., "Inflammatory bone loss: pathogenesis and therapeutic intervention", Nat Rev Drug Discov., Mar. 2012, 11(3): 234-250.

Regeneron Pharmaceuticals, Inc., "Sanofi And Regeneron Announce Patient Enrollment in Two Phase 3 Trials With Sarilumab in Rheumatoid Arthritis (RA)", Online Publication, May 15, 2013 at 1:00 AM EDT.

Roche, Anti-Human IL-6 Receptor Monoclonal Antibody "Actemra" Subcutaneous Injection Demonstrates Efficacy in Rheumatoid Arthritis in Phase III Clinical Study, Jul. 19, 2011, Retrieved online: <URL: https://www.roche.com/dann/jcr:c49f4e4e-d60e-48cc-a14e-c0f1f4107b24/en/inv-update-2011-07-19b-annex.pdf>, Retrieved on Feb. 8, 2022.

Salaffi et al. "The health-related quality of life in rheumatoid arthritis, ankylosing spondylitis, and psoriatic arthritis: a comparison with a selected sample of healhty people", Health and Quality of Life Outcomes, Biomed Central, vol. 7, No. 1, pp. 25, 2009.

Schett, "Physiological Effects of Modulating the Interleukin-6 Axis", Rheumatology, vol. 57, Supplement 2, pp. ii43-ii50, Feb. 1, 2018.

Schett, et al., "Bone Erosion in Rheumatoid Arthritis: Mechanisms, Diagnosis and Treatment", Nature Reviews Rheumatology, vol. 8, No. 11, 22 Pages, Nov. 2012.

Sebba et al., "Comparative Effectiveness of TNF Inhibitor vs IL-6 Receptor Inhibitor as Monotherapy or Combination Therapy with Methotrexate in Patients with Rheumatoid Arthritis: Analysis from the CorEvitas RA Registry", Poster No. 0834, ACR Convergence—Virtual, Nov. 1-10, 2021.

Sebba, "Comparative Effectiveness of TNF Inhibitor vs IL-6 Receptor Inhibitor as Monotherapy or Combination Therapy with Methotrexate in Patients with Rheumatoid Arthritis: Analysis from the CorEvitas RA Registry", SAR-54318 TNFi/IL-6Ri Mono/Combo Audio narration, ACR Convergence—Virtual, Nov. 1-10, 2021.

Sechidis, et al., "Distinguishing Prognostic and Predictive Biomarkers: An Information Theoretic Approach", Bioinformatics, vol. 34, No. 19, pp. 3365-3376, Oct. 1, 2018.

Singh, et al., 2015 American College of Rheumatology Guideline for the Treatment of Rheumatoid Arthritis, Arthritis & rheumatology, vol. 68, No. 1, pp. 1-26, 2016.

Smolen et al., "Rheumatoid arthritis", Lancet, 2016, 388(10055): 2023-2038.

Smolen, et al., "The Assessment of Disease Activity in Rheumatoid Arthritis", Clinical and Experimental Rheumatology, vol. 28, Supplement 59, pp. S18-S27, May 1, 2010.

Smolen, et al., Eular Recommendations for the Management of Rheumatoid Arthritis With Synthetic and Biological Disease-modifying Antirheumatic Drugs: 2016 Update, Annals of the Rheumatic Diseases, vol. 76, No. 6, pp. 960-977, 2017.

Solomon, et al., "Patterns of Cardiovascular Risk in Rheumatoid Arthritis", Annals of the Rheumatic Diseases, vol. 65, pp. 1608-1612, Dec. 1, 2006.

Song, et al., "Comparative Evaluation of the Effects of Treatment With Tocilizumab and TNF-α Inhibitors on Serum Hepcidin, Anemia Response and Disease Activity in Rheumatoid Arthritis Patients", Arthritis Research & Therapy, vol. 15, Article No. R141, pp. 1-10, Oct. 1, 2013.

Stamp et al., "The use of low dose methotrexate in rheumatoid arthritis—are we entering a new era of therapeutic drug monitoring and pharmacogenomics?", Biomedicine & Pharmacotherapy, 2006, 60: 678-687.

(56) References Cited

OTHER PUBLICATIONS

Strand et al., "Patient-reported outcomes from a randomized phase III trial of sarilumab monotherapy versus adalimumab monotherapy in patients with rheumatoid arthritis", Arthritis Res Ther., 2018, 20(1): 129.
Study of the Safety, Tolerability, and Bioactivity of Tocilizumab on Patients With Non-infectious Uveitis, The Stop-Uveitis Study, ClinicalTrials.gov Archive, Oct. 29, 2012.
Świerkot et al., "Methotrexate in rheumatoid arthritis", Pharmacological Reports, 2006, 58: 473-492.
Taylor, et al., "A Transgenic Mouse That Expresses a Diversity of Human Sequence Heavy and Light Chain Immunoglobulins", Nucleic Acids Research, vol. 20, No. 23, pp. 6287-6295, Dec. 11, 1992.
United States Census Bureau. Census Regions and Divisions of the United States, Retrieved from: «https://www2.census.gov/geo/pdfs/maps-data/maps/reference/us_regdiv.pdf», Accessed on: Apr. 8, 2019.
Van Herwaarden, et al., Dose Reduction of Tocilizumab in Rheumatoid Arthritis Patients With Low Disease Activity, Clinical and Experimental Rheumatology, vol. 32, pp. 390-394, 2014.
Van Vollenhoven, Sex Differences in Rheumatoid Arthritis: More Than Meets the Eye, BMC Medicine, vol. 7, No. 12, pp. 1-4, Mar. 30, 2009.
Wei et al., "Serum Levels of IL-6 and TNF-α May Correlate with Activity and Severity of Rheumatoid Arthritis", Med Sci Monit., 2015, 21: 4030-4038.
Wells, et al., "Immunogenicity of Sarilumab Monotherapy in Patients with Rheumatoid Arthritis Who Were Inadequate Responders or Intolerant to Disease-Modifying Antirheumatic Drugs", Rheumatology and Therapy, vol. 6, No. 3, pp. 339-352, May 14, 2019.
Yokota et al., "Efficacy and safety of tocilizumab in patients with systemic-onset juvenile idiopathic arthritis: a randomised, double-blind, placebo-controlled, withdrawal phase III trial", The Lancet, Mar. 22, 2008, 371(9617): pp. 998-1006.
2011) International Nonproprietary Names (INN) for Pharmaceutical Substances, World Health Organization, vol. 25, No. 4, 53 Pages.
Apr. 13, 2015) Phase II Study to Analyze Sarilumab in Non-Infectious Uveitis, NCT01900431 on Apr. 13, 2015, ClinicalTrials.gov Archive, URL: https://clinicaltrials.gov/archive/NCT01900431.
Oct. 29, 2010) Study of the Safety, Tolerability, and Bioactivity of Tocilizumab on Patients with Non-infectious Uveitis: The Stop-Uveitis Study (Stop-Uveitis), Available at: https://clinicaltrials.gov/ct2/show/NCT01717170.
Oct. 29, 2012) Study of the Safety, Tolerability, and Bioactivity of Tocilizumab on Patients with Non-infectious Uveitis, The Stop-Uveitis Study, ClinicalTrials.gov Archive.
Adan, et al. (Jul. 27, 2013) "Tocilizumab Treatment for Refractory Uveitis-Related Cystoid Macular Edema", Graefes Archive for Clinical and Experimental Ophthalmology, vol. 251, No. 11, pp. 2627-2632.
Advisory Action received for U.S. Appl. No. 13/648,521, mailed on Jul. 19, 2016, 3 Pages.
Aletaha, et al. (Sep. 2010) "Rheumatoid Arthritis Classification Criteria: An American College of Rheumatology/European League Against Rheumatism Collaborative Initiative", Arthritis and Rheumatology, vol. 62, No. 9, pp. 2569-2581.
Amit, et al. (Aug. 15, 1986) "Three-Dimensional Structure of An Antigen-Antibody Complex at 2.8 A Resolution", Science, vol. 233, No. 4765, pp. 747-753.
An, et al. (Jan. 2010) "The Addition of Tocilizumab to Dmard Therapy for Rheumatoid Arthritis: A Meta-Analysis of Randomized Controlled Trials", European Journal of Clinical Pharmacology, vol. 66, No. 1, pp. 49-59.
Angal et al., "A single amino acid substitution abolishes the heterogeneity of chimeric mouse/human (IgG4) antibody", Molecular Immunology, Jan. 1993, 30(1): 105-108.
Arevalo, J Fernando, (Nov. 25, 2014) "Tocilizumab Shows Promise for Refractory Uveitis-Related Macular Edema", URL: https://www.aao.org/editors-choice/tocilizumab-shows-promise-refractory-uveitisrelate.

Barry, et al. (Sep. 1, 2014) "Pharmacotherapy for Uveitis: Current Management and Emerging Therapy", Clinical Ophthalmology, vol. 8, pp. 1891-1911.
Bresnick, George H. (Jul. 1986) "Diabetic Macular Edema. A Review.", Ophthalmology, vol. 93, Issue 7, pp. 989-997.
Burmester, et al. (Jan. 2014) "A Randomised, Double-Blind, Parallel-Group Study of the Safety and Efficacy of Subcutaneous Tocilizumab Versus Intravenous Tocilizumab in Combination with Traditional Disease-Modifying Antirheumatic Drugs in Patients with Moderate to Severe Rheumatoid Arth", Annals of the Rheumatic Diseases, vol. 73, No. 1, pp. 69-74.
Burmester, et al. (May 2017) "Efficacy and Safety of Sarilumab Monotherapy Versus Adalimumab Monotherapy for The Treatment of Patients with Active Rheumatoid Arthritis (Monarch): A Randomised, Double-Blind, Parallel-Group Phase III Trial", Annals of the Rheumatic Diseases, vol. 76, No. 5, pp. 840-847.
Bykerk et al., "Impact of Sarilumab on Unacceptable Pain and Inflammation Control in Moderately-to-Severely Active Rheumatoid Arthritis (RA) Patients in 3 Phase 3 Studies", Arthritis & Rheumatology (Hoboken), Oct. 1, 2019, 71(S10): Abstract No. 1393.
Bykerk et al., "Impact of sarilumab on unacceptable pain and inflammation control in moderately-to-severely active rheumatoid arthritis (RA) patients in 3 Phase 3-studies", Rheumatology, Apr. 20, 2020, 59(2): EP25.
Bykerk et al., "Impact of Sarilumab on Unacceptable Pain and Inflammation Control in Moderately-to-Severely Active Rheumatoid Arthritis Patients in 3 Phase 3 Studies", Sep. 11, 2020, retrieved from url: https://pheedloop.s3.amazonaws.com/media/events/EVEVLUEFMPIXU/files/822199_Bykerk-Vivian-RA-Unacceptable%20Pain.pdf.
Cao, et al. (Jun. 2013) "Pharmacological Blockade of Interleukin 6 Receptor (IL-6R) Inhibits the Development of Ocular Inflammation in the Murine Model of Experimental Autoimmune Uveitis (EAU)", Investigative Ophthalmology & Visual Science, vol. 54, Issued 15, 5193 Page.
Chester (Jul. 24, 2017) E-mail: "<External> CAS Registry No. RN1189541-98-7".
Chichasova, et al. (2010) "Treatment of Rheumatoid Arthritis: Tactical Issues in the Practice of the Clinician", The Attending Physician, No. 7/10.
Choy et al., "Indirect Treatment Comparison of the Efficacy and Safety of Sarilumab Monotherapy in Rheumatoid Arthritis Patients with Inadequate Response to Conventional Disease-Modifying Antirheumatic Drugs", Advances in Therapy, Mar. 12, 2019, 36(4): 817-827.
ClinicalTrials.gov, "Efficacy and Safety of Sarilumab and Adalimumab Monotherapy in Patients With Rheumatoid Arthritis (Saril-RA-Monarch)", ClinicalTrials.gov Identifier NCT02332590, Jan. 7, 2015.
Clinicaltrials.gov, "Evaluation of Sarilumab (SAR153191/REGN88) on Top of Methotrexate in Rheumatoid Arthritis Patients (RA-Mobility)", ClinicalTrials.gov Identifier NCT01061736, Feb. 3, 2010.
Clinicaltrials.gov, "To Evaluate The Effect of SAR153191 (REGN88) Added to Other RA Drugs in Patients With RA Who are not Responding to or Intolerant of Anti-TNF Therapy (Saril-RA-Target)", ClinicalTrials.gov Identifier NCT01709578, Oct. 18, 2012.
Daugherty et al., "Formulation and delivery issues for monoclonal antibody therapeutics," Adv. Drug Delivery Reviews, 58:686-706, (2006).
Davis, et al. (Nov. 2010) "Scale for Photographic Grading of Vitreous Haze in Uveitis", American Journal of Ophthalmology, vol. 150, No. 5, pp. 637-641. Pharmacology of TNF blockade.
Durrani, et al. (Sep. 2004) "Degree, Duration, and Causes of Visual Loss in Uveitis", British Journal of Ophthalmology, vol. 88, No. 9, pp. 1159-1162.
Emery, et al. (Nov. 2008) "IL-6 Receptor Inhibition with Tocilizumab Improves Treatment Outcomes in Patients with Rheumatoid Arthritis Refractory to Anti-Tumour Necrosis Factor Biologicals: Results From a 24-Week Multicentre Randomised Placebo-Controlled Trial", Annals of the Rheumatic Diseases, vol. 67, No. 11, pp. 1516-1523.

(56) References Cited

OTHER PUBLICATIONS

European Medicines Agency, Committee for Medicinal Products for Human Use (CHMP), Assessment Report, Apr. 21, 2017, EMA/292840/2017, retrieved from url: https://www.ema.europa.eu/en/documents/assessment-report/kevzara-epar-public-assessment-report_en.pdf.

Final Office Action received for U.S. Appl. No. 13/648,521, mailed on Mar. 10, 2014, 9 Pages.

Final Office Action received for U.S. Appl. No. 13/648,521, mailed on Feb. 11, 2016, 13 Pages.

Fleischmann, et al. (Oct. 2014) "Comparable Efficacy with Sarilumab Plus Methotrexate in Biologic-Experienced and Biologic-Naïve Patients with Moderate-to-Severe Rheumatoid Arthritis from a Phase 3, Randomized, Double-Blind, Placebo-Controlled, International Study", Arthritis & Rheumatology, vol. 66, No. S10, pp. S1232.

Fransen et al., "The Disease Activity Score and the Eular response criteria", Clinical and Experimental Rheumatology, Aug. 31, 2005, 23(5 Suppl 39): S93-99).

Gandek, et al. (Summer 2004) "Psychometric Evaluation of the SF-36® Health Survey in Medicare Managed Care", Health Care Financing Review, vol. 25, No. 4, pp. 5-25.

Genentech, et al. (2014) "Acterma Subcutaneous Dosing & Administration Pocket Guide", pp. 1-40.

Genovese, et al. (Jun. 2015) "Sarilumab Plus Methotrexate in Patients with Active Rheumatoid Arthritis and Inadequate Response to Methotrexate: Results of a Phase III Study", Arthritis & Rheumatology, vol. 67, No. 6, pp. 1424-1437.

Gordon, et al. (Jul. 1998) "pANCA Antibodies in Patients with Anterior Uveitis: Identification of A Marker Antibody Usually Associated with Ulcerative Colitis", Journal of Clinical Immunology, vol. 18, No. 4, pp. 264-271.

HAQ (Jul. 30, 2019) "Scleroderma Study Conference", English Translation, Retrieved from URL: <http://derma.w3.kanazawa-u.ac.jp/SSc/pamphret/HAQ.html », 6 Pages (4 Pages of English Translation & 2 Pages of Official Copy).

Hennigan, et al. (Aug. 2008) "Interleukin-6 Inhibitors in the Treatment of Rheumatoid Arthritis", Therapeutics and clinical risk management, vol. 4, No. 4, pp. 767-775.

Hirata, et al. (Nov. 1, 1989) "Characterization of IL-6 Receptor Expression by Monoclonal and Polyclonal Antibodies", The Journal of Immunology, vol. 143, No. 9, pp. 2900-2906.

Huizinga, et al. (Sep. 2014) "Sarilumab, A Fully Human Monoclonal Antibody Against IL-6Rα in Patients with Rheumatoid Arthritis and an Inadequate Response to Methotrexate: Efficacy and Safety Results from the randomised Saril-RA-Mobility Part A Trial", Annals of the Rheumatic Diseases, vol. 73, No. 9, pp. 1626-1629.

International Search report and Written Opinion for PCT International Patent Application No. PCT/US2020/035871, 13 pages.

International Search Report and Written Opinion received for PCT Patent Application No. PCT/EP2012/070052, mailed on Jan. 10, 2013, 10 Pages.

International Search Report and Written Opinion received for PCT Patent Application No. PCT/US2014/066856, mailed on Apr. 2, 2015, 11 Pages.

International Search Report and Written Opinion received for PCT Patent Application No. PCT/US2015/050291, mailed on Dec. 1, 2015, 12 Pages.

International Search Report and Written Opinion received for PCT Patent Application No. PCT/US2016/060344, mailed on Mar. 13, 2017, 13 pages.

International Search Report and Written Opinion received for PCT Patent Application No. PCT/US2017/021149, mailed on Jul. 18, 2017, 14 Pages.

Kawashima, et al. (Apr. 6, 2007) "Soluble IL-6 Receptor in Vitreous Fluid of Patients with Proliferative Diabetic Retinopathy", Japanese Journal of Ophthalmology, vol. 51, No. 2, pp. 100-104.

Kishimoto, et al. (2003) "Interleukin-6 (IL-6)", The Cytokine Handbook. Ed.: Thomson. Academic Press. London, United Kingdom, vol. 12, pp. 281-304.

Kivitz, et al. (Nov. 2014) "Subcutaneous Tocilizumab Versus Placebo in Combination with Disease-Modifying Antirheumatic Drugs in Patients with Rheumatoid Arthritis", Rheumatoid Arthritis, vol. 66, Issue 11, pp. 1653-1661.

Langer, Robert (Sep. 28, 1990) "New Methods of Drug Delivery", Science, vol. 249, Issue 4976, pp. 1527-1533.

Lederman, et al. (Nov. 1991) "Single Amino Acid Substitution in a Common African Allele of The CD4 Molecule Ablates Binding of The Monoclonal Antibody, OKT4", Molecular Immunology, vol. 28, No. 11, pp. 1171-1181.

Li, et al. (May 2004) "Temporal Associations Between Interleukin 22 and the Extracellular Domains of IL-22R and IL-1 OR2", International Immunology, vol. 4, No. 5, pp. 693-708.

Lin, Phoebe (Sep. 1, 2015) "Targeting Interleukin-6 for Noninfectious Uveitis", Clinical Ophthalmology, vol. 9, pp. 1697-1702.

Lipsky, Peter E. (2006) "Interleukin-6 and Rheumatic Diseases", Arthritis Research & Therapy, vol. 8, Suppl 2, S4, pp. 1-5.

Lourdudoss et al., "Dietary intake of polyunsaturated fatty acids and pain in spite of inflammatory control among methotrexate-treated early rheumatoid arthritis patients", Arthritis Care and Research, Feb. 2018, 70(2): 205-212.

McGovern, Timothy J. (Oct. 19, 2016) "Center for Drug Evaluation and Research", Application No. 761037Orig1s000, pp. 01-278.

Meehan, et al. (May 5, 1997) "A Microinfusor Device for the Delivery of Therapeutic Levels of Peptides and Macromolecules", Journal of Controlled Release, vol. 46, Issues 1-2, pp. 107-116.

Merida, et al. (Aug. 11, 2015) "New Immunosuppressive Therapies in Uveitis Treatment", International Journal of Molecular Sciences, vol. 16, No. 8, pp. 18778-18795.

Mesquida, et al. (Sep. 6, 2014) "Long-Term Effects of Tocilizumab Therapy for Refractory Uveitis-Related Macular Edema", Ophthalmology, vol. 121, No. 12, pp. 2380-2386.

Mihara, et al. (Nov. 2005) "Tocilizumab Inhibits Signal Transduction Mediated by Both mIL-6R and sIL-6R, But Not by The Receptors of Other Members of IL-6 Cytokine Family", International Immunopharmacology, vol. 5, No. 12, pp. 1731-1740.

Muszbek et al., "Economic Evaluation of Sarilumab in the Treatment of Adult Patients with Moderately-to-Severely Active Rheumatoid Arthritis Who Have an Inadequate Response to Conventional Synthetic Disease-Modifying Antirheumatic Drugs", Advances in Therapy, Apr. 19, 2019, 36(6): 1337-1357.

Nguyen, et al. (Jun. 2015) "The Saturn Study (Saril-NIU): Sarilumab for the Treatment of Posterior Segment Non-Infectious Uveitis (NIU)", Investigative Ophthalmology & Visual Science, vol. 56, No. 7, 3116 pages.

Nicassio, et al. (Jan. 2012) "The Contribution of Pain and Depression to Self-Reported Sleep Disturbance in Patients with Rheumatoid Arthritis", Pain, vol. 153, No. 1, pp. 107-112.

Nishimoto, et al. (Nov. 1, 2008) "Study of Active Controlled Tocilizumab Monotherapy for Rheumatoid Arthritis Patients with an Inadequate Response to Methotrexate (Satori): Significant Reduction in Disease Activity and Serum Vascular Endothelial Growth Factor by IL-6 Receptor Inhibition Th", Modern Rheumatology, vol. 19, No. 1, pp. 12-19.

Non-Final Office Action received for U.S. Appl. No. 13/648,521, mailed on Jul. 3, 2014, 12 Pages.

Non-Final Office Action received for U.S. Appl. No. 13/648,521, mailed on Jun. 26, 2015, 9 Pages.

Non-Final Office Action received for U.S. Appl. No. 13/648,521, mailed on Mar. 19, 2015, 8 Pages.

Non-Final Office Action received for U.S. Appl. No. 13/648,521, mailed on Oct. 18, 2013, 10 Pages.

Non-Final Office Action received for U.S. Appl. No. 14/350,973, mailed on Feb. 5, 2016, 18 Pages.

Non-Final Office Action received for U.S. Appl. No. 14/350,973, mailed on Oct. 18, 2019, 10 Pages.

Notice of Allowance received for U.S. Appl. No. 14/350,973, mailed on Jun. 14, 2016, 8 Pages.

Nussenblatt, et al. (Apr. 1985) "Standardization of Vitreal Inflammatory Activity in Intermediate and Posterior Uveitis", Ophthalmology, vol. 92, No. 4, pp. 467-471.

(56) References Cited

OTHER PUBLICATIONS

Ongkosuwito, et al. (Dec. 1998) "Analysis of Immunoregulatory Cytokines in Ocular Fluid Samples from Patients with Uveitis", Investigative Ophthalmology & Visual Science, vol. 39, No. 13, pp. 2659-2665.
Panka, et al. (May 1988) "Variable Region Framework Differences Result in Decreased or Increased Affinity of Variant Anti-Digoxin Antibodies", Proceedings of the National Academy of Sciences of the United States of America, vol. 85, pp. 3080-3084.
Patro et al., "Protein formulation and fill-finish operations," Biotechnol Annu Rev, 8:55-84, (2002). Abstract only.
Paul-Pletzer (2006) "Tocilizumab: Blockade of Interleukin-6 Signaling Pathway as a Therapeutic Strategy for Inflammatory Disorders", Drugs of Today, vol. 42, No. 9, pp. 559-576.
Peichl, "Biologikatherapie in der Rheumatologie", DoctorConsult—The Journal. Wissen fur Klinik und Praxis, Nov. 2011, 2(3): e164-e166.
Perez, et al. (Sep. 2004) "Elevated Levels of Interleukin 6 in the Vitreous Fluid of Patients with Pars Planitis and Posterior Uveitis: The Massachusetts Eye & Ear Experience and Review of Previous Studies", Ocular Immunology and Inflammation, vol. 12, No. 3, pp. 193-201.
Pham et al., "Patient acceptable symptomatic state (PASS)", Joint Bone Spine, Jul. 2009, 76(4): 321-323.
Powchik (Jul. 15, 2010) "Investor Day", Regeneron Pharmaceuticals, pp. 1-19.
Powell, et al. (Sep.-Oct. 1998) "Compendium of Excipients for Parenteral Formulations", PDA Journal of Pharmaceutical Science and Technology, vol. 52, No. 5, pp. 238-311.
Presta (2006) "Engineering of Therapeutic Antibodies to Minimize Immunogenicity and Optimize Function", Advanced Drug Delivery Reviews, pp. 640-656.
PubChem SID: 135626879, National Library of Medicine, https://pubchem.ncbi.nlm.nih.gov/substance/135626879, Apr. 5, 2012.
Radin, et al. (Jan. 1, 2010) "Safety and Effects on Markers of Inflammation of Subcutaneously Administered regn88/sar153191 (regn88), an Interleukin-6 Receptor Inhibitor, in Patients with Rheumatoid Arthritis: Findings from Phase 1 Studies", Annals of the Rheumatic Diseases, vol. 69, Supplement 3, XP008158577, 99 Page.
Radin, et al. (Nov. 2010) "REGN88/SAR153191, a fully-human interleukin-6 receptor monoclonal antibody, reduces acute phase reactants in patients with rheumatoid arthritis: preliminary observations from Phase 1 studies.", Arthritis & Rheumatology, vol. 62, Supplement 10, XP008158581, p. S1121.
Rafique, et al. (Jun. 23, 2013) "Evaluation of The Binding Kinetics and Functional Bioassay Activity of Sarilumab and Tocilizumab to The Human IL-6 Receptor (IL-6r) alpha", Annals of the Rheumatic Diseases, vol. 72, Issue Suppl 3, pp. A797.1-A797.
Raimondo et al., "Profile of sarilumab and its potential in the treatment of rheumatoid arthritis", Drug Design, Development and Therapy, May 24, 2017, 11: 1593-1603.
Reddy et al., "Elimination of Fc Receptor-Dependent Effector Functions of a Modified IgG4 Monoclonal Antibody to Human CD4," Journal of Immunology, 164:1925-1933 (2000).
Regeneron (Jun. 12, 2014) "Sanofi and Regeneron Announce New, Detailed Data from Positive Sarilumab Phase 3 Rheumatoid Arthritis Trial at Eular".
Regeneron (Nov. 22, 2013) "Sanofi and Regeneron Report Positive Results with Sarilumab in First Phase 3 Rheumatoid Arthritis Registration Trial", Press Release, Acquire Media, Retrieved From: «https://investor.regeneron.com/news-releases/news-release-details/sanofi-and-regeneron-report-positive-results-sarilumab-first», 6 pages.
Regeneron Pharmaceuticals (Jul. 12, 2011) "Evaluation of Sarilumab (SAR153191/REGN88) on Top of Methotrexate in Rheumatoid Arthritis Patients (RA-Mobility)", Retrieved from the internet from URL «https://clinicaltrials.gov/ct2/results?term=SAR+153191=mobility».
Regeneron Pharmaceuticals (Jul. 12, 2011) "Sanofi and Regeneron Report Positive Phase 2b Trial Results with Sarilumab in Rheumatoid Arthritis", Acquire Media, Retrieved form URL: <http://web.archive.org/web/20110818152737/http://investorregeneron.com/released etail.cfm?ReleaseiD=590869», 3 pages.
Reichert, Janice M. (Jan.-Feb. 2011) "Antibody-Based Therapeutics to Watch in 2011", MABS, vol. 3, No. 1, pp. 76-99.
Restriction Requirement received for U.S. Appl. No. 13/648,521, mailed on Jun. 10, 2013, 7 Pages.
Restriction Requirement received for U.S. Appl. No. 14/350,973, mailed on Aug. 19, 2015, 8 Pages.
Riancho-Zarrabeitia, et al., "Efficacy of Tocilizumab in Patients with Uveitis Refractory to Other Biologic Drugs: A Multicenter Study on 31 Cases", 2014 ACR/ARHP Annual Meeting Abstract No. 1249, Retrieved from: «https://acrabstracts.org/abstract/efficacy-of-Tocilizumab-in-patients-with-uveitis-refractory-to-other-biologic-drugs-a-multicenter-study-on-31-cases/».
Rose-John, et al. (May 17, 2006) "Interleukin-6 Biology is Coordinated by Membrane-Bound and Soluble Receptors: Role in Inflammation and Cancer", Journal of Leukocyte Biology, vol. 80, No. 2, pp. 227-236.
Rudikoff, et al. (Mar. 1, 1982) "Single Amino Acid Substitution Altering Antigen-Binding Specificity", Proceedings of the National Academy of Sciences of the United States of America, vol. 79, pp. 1979-1983.
Sanofi (Feb. 2, 2010) "Evaluation of Sarilumab (SAR153191/REGN88) on Top of Methotrexate in Rheumatoid Arthritis Patients (RA-Mobility)", Clinical Trials.gov, Retrieved from: «http://clinicaltrials.gov/show/NCT01061736», 6 pages.
Sanofi (Nov. 7, 2013) "View of NCT01061736 on Nov. 7, 2013: ClinicaiTrials.gov Archive", Retrieved from URL: «https://clinicaltrials.gov/archive/NCT01061736/2013_11_07».
Sanofi (Oct. 7, 2010) "Effect of SAR153191 (REGN88) With Methotrexate in Patients with Active Rheumatoid Arthritis Who Failed TNF-α Blockers", ClinicaiTrials.gov, Retrieved from: «http://clinicaltrials.gov/show/NCT01217814», 5 pages.
Sanofi (Sep. 27, 2011) "View of NCT01217814 on Sep. 27, 2011", ClinicaiTrials.gov, Retrieved from URL: «https://clinicaltrials.gov/archive/NCT01217814/2011_09_27», 4 pages.
Sanofi and Regeneron (May 21, 2015) "Sanofi and Regeneron Announce Positive Topline Results from Phase 3 Studies with Sarilumab in Patients with Rheumatoid Arthritis", Press Release, Retrieved from http://mediaroom.sanofi.com/sanofi-and-regeneron-announce-positive-topline-results-from-phase-3-studies-witharilumab-in-patients-with-rheumatoid-arthritis-2, 4 pages.
Sanofi and Regeneron (Nov. 8, 2015) "Regeneron and Sanofi Present Results from Pivotal Phase 3 Study of Sarilumab at American College of Rheumatology Annual Meeting", Press Release, Regeneron Pharmaceuticals, Inc. Retrieved from http://investor.regeneron.com/releasedetail.cfm?releaseid=941387.
Shields et al., "Lack of Fucose on Human IgG1 N-Linked Oligosaccharide Improves Binding to Human Fc gamma RIII and Antibody-dependent Cellular Toxicity," Journal of Biological Chemistry, 277(30):26733-26740 (2002).
Smolen, et al. (Mar. 22-28, 2008) "Effect of Interleukin-6 Receptor Inhibition with Tocilizumab in Patients with Rheumatoid Arthritis (Option Study): A Double-Blind, Placebo-Controlled, Randomised Trial", The Lancet, vol. 371, Issue 9617, pp. 987-997.
Strand, et al. (2012) "Health-related Quality of Life Outcomes of Adalimumab for Patients with Early Rheumatoid Arthritis: Results from a Randomized Multicenter Study", The Journal of Rheumatology, vol. 39, pp. 63-72.
Suttorp-Schulten, et al. (1996) "Recent Developments in the Treatment of Posterior Uveitis", Ocular Immunology and Inflammation, vol. 4, No. 4, pp. 207-217.
Taylor et al., "A transgenic mouse that expresses a diversity of human sequence heavy and light chain immunoglobulins", Nucleic Acids Research, Dec. 11, 1992, 20(23): 6287-6295.
Taylor, Peter C. (Jun. 2010) "Pharmacology of TNF Blockade in Rheumatoid Arthritis and Other Chronic Inflammatory Diseases", Current Opinion in Pharmacology, vol. 10, Issue 3, pp. 308-315.
The Chemical Abstracts Service CAS, 1189541-98-7, (2015).
U.S. Adopted Names Council "Statement on a Nonproprietary Name Adopted by the USAN Council: Sarilumab", CAS Registry No. 1189541-98-7, (2013).

(56) References Cited

OTHER PUBLICATIONS

Uchiyama, et al. (2008) "Tocilizumab, A Humanized Anti-Interleukin-6 Receptor Antibody, Ameliorates Joint Swelling in Established Monkey Collagen-Induced Arthritis", Biological and Pharmaceutical Bulletin, vol. 31, No. 6, pp. 1159-1163.
Valentincic, et al. (Jul. 20, 2011) "Intraocular and Serum Cytokine Profiles in Patients with Intermediate Uveitis", Molecular Vision, vol. 17, pp. 2003-2010.
Vasanthi, et al. (Dec. 2007) "Role of Tumor Necrosis Factor-Alpha in Rheumatoid Arthritis: A Review", APLAR Journal of Rheumatology, vol. 10, No. 4, pp. 270-274.
Wang et al., "MiniReview: Antibody Structure, Instability, and Formulation," Journal of Pharmaceutical Sciences, 96(1):1-26, (2007).
Wang, "Instability, stabilization, and formulation of liquid protein pharmaceuticals," Int'l J. Pharmaceutics, 185(2):129-188, (1999).
Whalley, et al. (1997) "Quality of Life in Rheumatoid Arthritis", British Journal of Rheumatology, vol. 36, pp. 884-888.
Wiens, et al. (Jun. 2010) "A Systematic Review and Meta-Analysis of the Efficacy and Safety of Adalimumab for Treating Rheumatoid Arthritis", Rheumatology International, vol. 30, Issue 8, pp. 1063-1070.
Wu, et al. (Apr. 5, 1987) "Receptor-Mediated In Vitro Gene Transformation by a Soluble DNA Carrier System", Journal of Biological Chemistry, vol. 262, No. 10, pp. 4429-4432.
Yoshimura, et al. (2009) "Comprehensive Analysis of Inflammatory Immune Mediators in Vitreoretinal Diseases", PLoS One, vol. 4, No. 12, pp. 1-9.
Choy et al., "Subcutaneous tocilizumab in rheumatoid arthritis: findings from the common-frame work phase 4 study programme Tozura conducted in 22 countries", Rheumatology, Mar. 1, 2018, 57(3): 499-507.
ClinicalTrials.gov. (Jan. 17, 2017) "A Study of the Efficacy and Safety of Tocilizumab in Adults With Rheumatoid Arthritis", ClinicalTrials.gov. Identifier: NCT01988012.
ClinicalTrials.gov. (May 11, 2016) "A Study to Compare Subcutaneous Versus Intravenous Administration of RoActemra/Actemra (Tocilizumab) in Participants With Moderate to Severe Active Rheumatoid Arthritis", ClinicalTrials.gov. Identifier: NCT01194414.
ClinicalTrials.gov. (Sep. 15, 2014) "Torpedo Study: A Study on Rapid Effect of Tocilizumab in Patients With Rheumatoid Arthritis With an Inadequate Response to Disease-Modifying Antirheumatic Drugs (DMARDs) or Anti-TNF", ClinicalTrials.gov. Identifier: NCT00977106.
Emery et al., "Evidence-based review of biologic markers as indicators of disease Progression and remission in rheumatoid arthritis", Rheumatol Int., Jul. 2007, 27(9): 793-806, Epublished May 16, 2007.
Huizen et al., "What does it mean if you have a high C-reactive protein level?", Medical News Today, Oct. 11, 2023.
Izumi et al., "Steroid-Sparing Effect of Tocilizumab and Methotrexate in Patients with Polymyalgia Rheumatica: A Retrospective Cohort Study", Journ Clin Med., Jun. 30, 2021, 10: 2948.
Ohta et al., "Mechanism-Based Approach Using a Biomarker Response to Evaluate Tocilizumab Subcutaneous Injection in Patients With Rheumatoid Arthritis With an Inadequate Response to Synthetic DMARDs (Matusri Study)", The Journal of Clinical Pharmacology, Jan. 2014, 54(1):109-119, Epublished Oct. 12, 2013.
Starkova et al., "ES02. Relationship between fatigue and IL 6, diseas activity, depression in patients treated with tocilizumab", Rheumatology, Feb. 2012, 51(Suppl 1): 134-i41, Published Jan. 10, 2012.
Starkova et al., "Impact of tocilizumab therapy on fatigue in patients with rheumatoid arthritis", Scientific and Practical Rheumatology, 2012, N 52(3): 33-37, English translation included.
Takeuchi, "Rheumatoid Arthritis: Advances in Diagnosis and Treatment", The Journal of the Japanese Society of Internal Medicine, 2012, vol. 101, pp. 2815-2817.
Unknown, "Differentiation of Arthritis: Advances in Diagnosis and Treatment 1. Rheumatoid Arthritis", The Journal of the Japanese Society of Internal Medicine, 2010, vol. 99, pp. 2392-2400.

\* cited by examiner

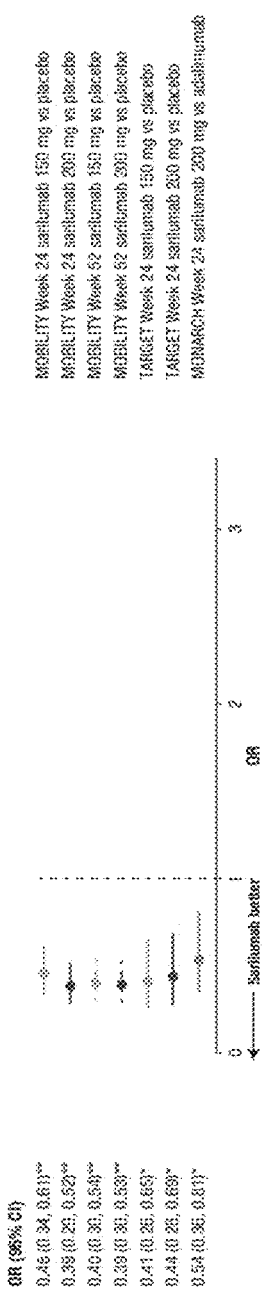
FIGURE 1A) Unacceptable pain
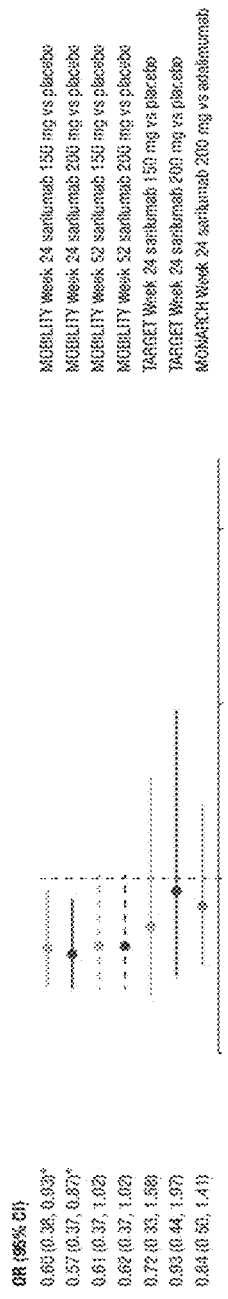
FIGURE 1B) Refractory pain despite inflammation control
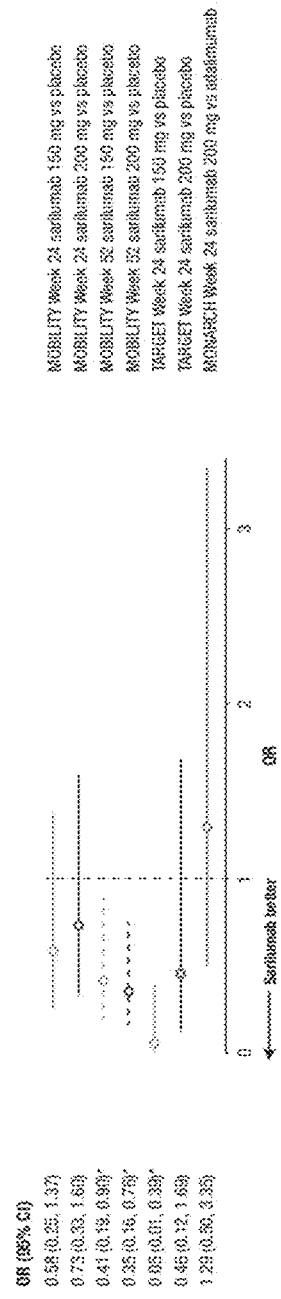
FIGURE 1C) Refractory pain-strict

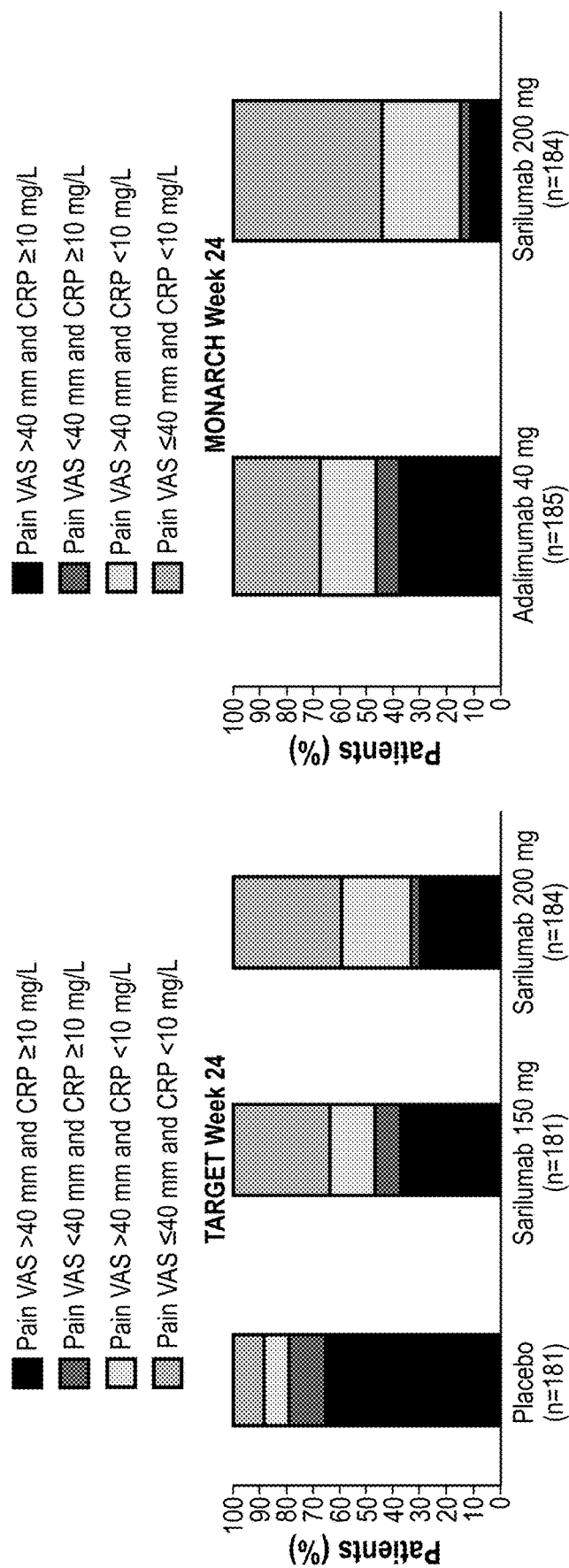

```
                        SEQUENCE LISTING

<160> NUMBER OF SEQ ID NOS: 11

<210> SEQ ID NO 1
<211> LENGTH: 116
<212> TYPE: PRT
<213> ORGANISM: Artificial Sequence
<220> FEATURE:
<223> OTHER INFORMATION: Heavy chain variable region

<400> SEQUENCE: 1

Glu Val Gln Leu Val Glu Ser Gly Gly Gly Leu Val Gln Pro Gly Arg
1               5                   10                  15

Ser Leu Arg Leu Ser Cys Ala Ala Ser Arg Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
        50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Light chain variable region

<400> SEQUENCE: 2

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

-continued

```
Glu Asp Phe Ala Ser Tyr Tyr Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 3
<211> LENGTH: 8
<212> TYPE: PRT
<213> ORGANISM: Artificial Sequence
<220> FEATURE:
<223> OTHER INFORMATION: HCDR1

<400> SEQUENCE: 3

Arg Phe Thr Phe Asp Asp Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: HCDR2

<400> SEQUENCE: 4

Ile Ser Trp Asn Ser Gly Arg Ile
1               5

<210> SEQ ID NO 5
<211> LENGTH: 9
<212> TYPE: PRT
<213> ORGANISM: Artificial Sequence
<220> FEATURE:
<223> OTHER INFORMATION: HCDR3

<400> SEQUENCE: 5

Ala Lys Gly Arg Asp Ser Phe Asp Ile
1               5

<210> SEQ ID NO 6
<211> LENGTH: 6
<212> TYPE: PRT
<213> ORGANISM: Artificial Sequence
<220> FEATURE:
<223> OTHER INFORMATION: LCDR1

<400> SEQUENCE: 6

Gln Gly Ile Ser Ser Trp
1               5

<210> SEQ ID NO 7
<211> LENGTH: 3
<212> TYPE: PRT
<213> ORGANISM: Artificial Sequence
<220> FEATURE:
<223> OTHER INFORMATION: LCDR2

<400> SEQUENCE: 7

Gly Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: LCDR3
```

<400> SEQUENCE: 8

Gln Gln Ala Asn Ser Phe Pro Tyr Thr
1               5

<210> SEQ ID NO 9
<211> LENGTH: 446
<212> TYPE: PRT
<213> ORGANISM: Artificial Sequence
<220> FEATURE:
<223> OTHER INFORMATION: Heavy chain

<400> SEQUENCE: 9

Glu Val Gln Leu Val Glu Ser Gly Gly Gly Leu Val Gln Pro Gly Arg
1               5                   10                  15

Ser Leu Arg Leu Ser Cys Ala Ala Ser Arg Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Arg Ile Gly Tyr Ala Asp Ser Val
        50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro 340                 345                 350
Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
                435                 440                 445

<210> SEQ ID NO 10
<211> LENGTH: 214
<212> TYPE: PRT
<213> ORGANISM: Artificial Sequence
<220> FEATURE:
<223> OTHER INFORMATION: Light chain

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ala Asn Ser Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 358
<212> TYPE: PRT
<213> ORGANISM: Artificial Sequence
<220> FEATURE:
<223> OTHER INFORMATION: Extracellular domain of hIL-6R

<400> SEQUENCE: 11

```
Met Val Ala Val Gly Cys Ala Leu Leu Ala Ala Leu Leu Ala Ala Pro
1               5                   10                  15
Gly Ala Ala Leu Ala Pro Arg Arg Cys Pro Ala Gln Glu Val Ala Arg
                20                  25                  30
Gly Val Leu Thr Ser Leu Pro Gly Asp Ser Val Thr Leu Thr Cys Pro
                35                  40                  45
Gly Val Glu Pro Glu Asp Asn Ala Thr Val His Trp Val Leu Arg Lys
        50                  55                  60
Pro Ala Ala Gly Ser His Pro Ser Arg Trp Ala Gly Met Gly Arg Arg
65                  70                  75                  80
Leu Leu Leu Arg Ser Val Gln Leu His Asp Ser Gly Asn Tyr Ser Cys
                85                  90                  95
Tyr Arg Ala Gly Arg Pro Ala Gly Thr Val His Leu Leu Val Asp Val
                100                 105                 110
Pro Pro Glu Glu Pro Gln Leu Ser Cys Phe Arg Lys Ser Pro Leu Ser
            115                 120                 125
Asn Val Val Cys Glu Trp Gly Pro Arg Ser Thr Pro Ser Leu Thr Thr
130                 135                 140
Lys Ala Val Leu Leu Val Arg Lys Phe Gln Asn Ser Pro Ala Glu Asp
145                 150                 155                 160
Phe Gln Glu Pro Cys Gln Tyr Ser Gln Glu Ser Gln Lys Phe Ser Cys
                165                 170                 175
Gln Leu Ala Val Pro Glu Gly Asp Ser Ser Phe Tyr Ile Val Ser Met
                180                 185                 190
Cys Val Ala Ser Ser Val Gly Ser Lys Phe Ser Lys Thr Gln Thr Phe
            195                 200                 205
Gln Gly Cys Gly Ile Leu Gln Pro Asp Pro Pro Ala Asn Ile Thr Val
                210                 215                 220
Thr Ala Val Ala Arg Asn Pro Arg Trp Leu Ser Val Thr Trp Gln Asp
225                 230                 235                 240
Pro His Ser Trp Asn Ser Ser Phe Tyr Arg Leu Arg Phe Glu Leu Arg
                245                 250                 255
Tyr Arg Ala Glu Arg Ser Lys Thr Phe Thr Thr Trp Met Val Lys Asp
                260                 265                 270
Leu Gln His His Cys Val Ile His Asp Ala Trp Ser Gly Leu Arg His
            275                 280                 285
Val Val Gln Leu Arg Ala Gln Glu Glu Phe Gly Gln Gly Glu Trp Ser
            290                 295                 300
Glu Trp Ser Pro Glu Ala Met Gly Thr Pro Trp Thr Glu Ser Arg Ser
305                 310                 315                 320
Pro Pro Ala Glu Asn Glu Val Ser Thr Pro Met Gln Ala Leu Thr Thr
                325                 330                 335
Asn Lys Asp Asp Asp Asn Ile Leu Phe Arg Asp Ser Ala Asn Ala Thr
                340                 345                 350
Ser Leu Pro Val Gln Asp
            355
```

COMPOSITIONS AND METHODS FOR TREATING PAIN IN SUBJECTS WITH RHEUMATOID ARTHRITIS

CROSS-REFERENCE TO RELATED APPLICATIONS

This application claims the benefit of U.S. Provisional Patent Application Ser. No. 62/857,247, filed Jun. 4, 2019, 62/930,966, filed Nov. 5, 2019, and European Patent Application No. 20305191.7, filed Feb. 27, 2020, the entire disclosures of which are hereby incorporated herein by reference.

FIELD

The present disclosure relates to the field of therapeutic treatment of unacceptable pain in subjects who have or who have had rheumatoid arthritis.

BACKGROUND

Pain is a core-set domain and a troubling symptom to patients with rheumatoid arthritis (RA), and may be directly related to inflammation. Unacceptable pain (UP) levels may persist in patients despite receiving treatment-induced inflammation control (IC), i.e. refractory pain (RP).

Sarilumab is an interleukin-6 receptor antagonist for treatment of adults with moderately to severely active RA with an inadequate response or intolerance to one or more disease-modifying antirheumatic drugs (DMARDs).

SUMMARY

This disclosure provides methods and compositions for treating unacceptable pain in a subject who has rheumatoid arthritis. In various embodiments, treating the subject comprises administering a therapeutically effective amount of an antibody that specifically binds IL-6R.

In various embodiments, the antibody that specifically binds to the IL-6 receptor comprises a heavy chain variable region sequence of SEQ ID NO: 1 and a light chain variable region sequence of SEQ ID NO: 2

In various embodiments, the antibody comprises a heavy chain variable region (VH) and a light chain variable region (VL), wherein the VH comprises the three complementarity determining regions (CDRs) found within the sequence of SEQ ID NO:1 and wherein the VL comprises the three CDRs found within the sequence of SEQ ID NO:2. In various embodiments, the anti-IL-6R antibody or antigen-binding fragment thereof comprises three HCDRs (i.e., HCDR1, HCDR2 and HCDR3) and three LCDRs (i.e., LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8.

In various embodiment, the antibody is sarilumab.

In various embodiments, the subject has refractory pain. In various embodiments, the subject has UP despite treatment-induced inflammation control. In various embodiments, the subject has UP despite a reduction in inflammation of at least about 10%, 15%, 20%, 25%, 30%, 35%, 40%, 45%, or 50% compared to when the subject was first treated with a DMARD. In various embodiments, the subject has UP despite a reduction in inflammation of from 10% to 25%, from 25% to 50%, from 50% to 75%, from 75% to 95%, or from 75% to 100% compared to when the subject was first treated with a DMARD. In various embodiments, the subject has UP despite a reduction in inflammation of at least about 10%, 15%, 20%, 25%, 30%, 35%, 40%, 45%, or 50% compared to when the subject was first treated with one or more DMARDs other than sarilumab. In various embodiments, the subject has UP despite a reduction in inflammation of from 10% to 25%, from 25% to 50%, from 50% to 75%, from 75% to 95%, or from 75% to 100% compared to when the subject was first treated with one or more DMARDs other than sarilumab. In various embodiments, the subject has strict refractory pain. In various embodiments, the subject experiences a reduction in visual analog scale (VAS) of less than 40 after 24 or 52 weeks of treatment.

In various embodiments, the antibody is administered subcutaneously. In various embodiments, the antibody is administered every week, or every two weeks. In various embodiments, the antibody is administered once every week or once every two weeks.

In various embodiments, the antibody is administered at a dose from about 150 mg to 200 mg. In various embodiments, the antibody is administered at a dose of about 150 mg or about 200 mg. In various embodiments, the antibody is administered at a dose from 150 mg to 200 mg. In various embodiments, the antibody is administered at a dose of 150 mg or 200 mg.

In various embodiments, the subject has rheumatoid arthritis. In various embodiments, the subject has moderately to severely active rheumatoid arthritis. In various embodiments, the subject has moderately active rheumatoid arthritis. In various embodiments, the subject has severely active rheumatoid arthritis.

In various embodiments, a subject has a Disease Activity Score (DAS) of from 3.2 to 5.1. In various embodiments, a subject has a DAS of greater than 5.1. In various embodiments, the subject has a DAS of 3.2 or more. In various embodiments, the subject has a DAS of from 5 to 6, from 5 to 7, from 5 to 8, from 5 to 9, from 5 to 10, or from 7.5 to 10. The DAS for a subject can readily be calculated by those in the art. Non-limiting descriptions relating to DAS are provided in Fransen and van Riel (Clin Exp Rheumatol. 2005 September-October; 23 (5 Suppl 39):593-9), the entire content of which is incorporated herein by reference.

In various embodiments, no other disease modifying antirheumatic drug (DMARD) is administered with the antibody. In various embodiments, at least one other DMARD is administered to the subject. In various embodiments, at least one other DMARD is administered to the subject concurrently with or at the same time as the antibody. In various embodiments, the subject was previously ineffectively treated for rheumatoid arthritis by administering at least one DMARD different from the antibody. In various embodiments, the subject is intolerant of one or more DMARDs, or wherein the subject is considered an inappropriate candidate for continued treatment with one or more DMARDs.

In various embodiments, the DMARD is an sDMARD. In various embodiments, the DMARD is methotrexate. In various embodiments, the DMARD is a TNF antagonist. In various embodiments, the TNF antagonist is selected from etanercept, infliximab, adalimumab, golimumab and certolizumab pegol.

In another aspect, provided herein is a method for treating unacceptable pain (UP) in a subject in need thereof, comprising selecting a subject who has rheumatoid arthritis and UP, and administering to the subject a therapeutically effective dose of an antibody that specifically binds IL-6 receptor.

In various embodiments, the antibody that specifically binds to the IL-6 receptor comprises a heavy chain variable region sequence of SEQ ID NO: 1 and a light chain variable region sequence of SEQ ID NO: 2

In various embodiments, the antibody comprises a heavy chain variable region (VH) and a light chain variable region (VL), wherein the VH comprises the three complementarity determining regions (CDRs) found within the sequence of SEQ ID NO:1 and wherein the VL comprises the three CDRs found within the sequence of SEQ ID NO:2. In various embodiments, the anti-IL-6R antibody or antigen-binding fragment thereof comprises three HCDRs (i.e., HCDR1, HCDR2 and HCDR3) and three LCDRs (i.e., LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8.

In various embodiment, the antibody is sarilumab.

In various embodiments, the subject has refractory pain. In various embodiments, the subject has treatment induced strict refractory pain. In various embodiments, the subject experiences a reduction in visual analog scale (VAS) of less than 40 after 24 or 52 weeks of treatment.

In various embodiments, the antibody is administered subcutaneously. In various embodiments, the antibody is administered every week, or every two weeks. In various embodiments, the antibody is administered once every week or once every two weeks.

In various embodiments, the antibody is administered at a dose from about 150 mg to 200 mg. In various embodiments, the antibody is administered at a dose of about 150 mg or about 200 mg. In various embodiments, the antibody is administered at a dose from 150 mg to 200 mg. In various embodiments, the antibody is administered at a dose of 150 mg or 200 mg.

In various embodiments, the subject has rheumatoid arthritis. In various embodiments, the subject has moderately to severely active rheumatoid arthritis. In various embodiments, the subject has moderately active rheumatoid arthritis. In various embodiments, the subject has severely active rheumatoid arthritis.

In various embodiments, no other disease modifying antirheumatic drug (DMARD) is administered with the antibody. In various embodiments, at least one other DMARD is administered to the subject. In various embodiments, at least one other DMARD is administered to the subject concurrently with or at the same time as the antibody. In various embodiments, the subject was previously ineffectively treated for rheumatoid arthritis by administering at least one DMARD different from the antibody. In various embodiments, the subject is intolerant of one or more DMARDs, or wherein the subject is considered an inappropriate candidate for continued treatment with one or more DMARDs.

In various embodiments, the DMARD is an sDMARD. In various embodiments, the DMARD is methotrexate. In various embodiments, the DMARD is a TNF antagonist. In various embodiments, the TNF antagonist is selected from etanercept, infliximab, adalimumab, golimumab and certolizumab pegol.

In a further aspect, provided herein is an antibody for use in treating unacceptable pain in a patient in need thereof who has rheumatoid arthritis, wherein the antibody specifically binds IL-6 receptor.

In various embodiments, the antibody that specifically binds to the IL-6 receptor comprises a heavy chain variable region sequence of SEQ ID NO: 1 and a light chain variable region sequence of SEQ ID NO: 2

In various embodiments, the antibody comprises a heavy chain variable region (VH) and a light chain variable region (VL), wherein the VH comprises the three complementarity determining regions (CDRs) found within the sequence of SEQ ID NO:1 and wherein the VL comprises the three CDRs found within the sequence of SEQ ID NO:2. In various embodiments, the anti-IL-6R antibody or antigen-binding fragment thereof comprises three HCDRs (i.e., HCDR1, HCDR2 and HCDR3) and three LCDRs (i.e., LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8.

In various embodiments, the antibody is sarilumab.

In various embodiments, the subject has refractory pain. In various embodiments, the subject has treatment induced strict refractory pain. In various embodiments, the subject experiences a reduction in visual analog scale (VAS) of less than 40 after 24 or 52 weeks of treatment.

In various embodiments, the antibody is administered subcutaneously. In various embodiments, the antibody is administered every week, or every two weeks. In various embodiments, the antibody is administered once every week or once every two weeks.

In various embodiments, the antibody is administered at a dose from about 150 mg to 200 mg. In various embodiments, the antibody is administered at a dose of about 150 mg or about 200 mg. In various embodiments, the antibody is administered at a dose from 150 mg to 200 mg. In various embodiments, the antibody is administered at a dose of 150 mg or 200 mg.

In various embodiments, the subject has rheumatoid arthritis. In various embodiments, the subject has moderately to severely active rheumatoid arthritis. In various embodiments, the subject has moderately active rheumatoid arthritis. In various embodiments, the subject has severely active rheumatoid arthritis.

In various embodiments, a subject has a Disease Activity Score (DAS) of from 3.2 to 5.1. In various embodiments, a subject has a DAS of greater than 5.1. In various embodiments, the subject has a DAS of 3.2 or more. In various embodiments, the subject has a DAS of from 5 to 6, from 5 to 7, from 5 to 8, from 5 to 9, from 5 to 10, or from 7.5 to 10. The DAS for a subject can readily be calculated by those in the art. Non-limiting descriptions relating to DAS are provided in Fransen and van Riel (Clin Exp Rheumatol. 2005 September-October; 23 (5 Suppl 39):593-9), the entire content of which is incorporated herein by reference.

In various embodiments, no other disease modifying antirheumatic drug (DMARD) is administered with the antibody. In various embodiments, at least one other DMARD is administered to the subject. In various embodiments, at least one other DMARD is administered to the subject concurrently with or at the same time as the antibody. In various embodiments, the subject was previously ineffectively treated for rheumatoid arthritis by administering at least one DMARD different from the antibody. In various embodiments, the subject is intolerant of one or more DMARDs, or wherein the subject is considered an inappropriate candidate for continued treatment with one or more DMARDs.

In various embodiments, the DMARD is an sDMARD. In various embodiments, the DMARD is methotrexate. In various embodiments, the DMARD is a TNF antagonist. In various embodiments, the TNF antagonist is selected from etanercept, infliximab, adalimumab, golimumab and certolizumab pegol.

BRIEF DESCRIPTION OF THE FIGURES

FIGS. 1A-1C are graphs showing the odds ratios of three different randomized clinical trials—MOBILITY, TARGET and MONARCH. FIG. 1A illustrates the odds ratios for unacceptable pain. FIG. 1B illustrates the odds ratios for unacceptable pain despite inflammation control (IC) or inflammation control-strict (IC-strict). FIG. 1C illustrates the odds ratios for refractory pain-strict.

FIGS. 2A-2C are graphs showing descriptive analysis of pain outcomes. FIG. 2A illustrates analysis of pain outcomes in MOBILITY (Week 24 and Week 52). FIG. 2B illustrates analysis of pain outcomes in TARGET (Week 24 and Week 52). FIG. 2C illustrates analysis of pain outcomes in MONARCH (Week 24 and Week 52).

DETAILED DESCRIPTION

Figure 2A:
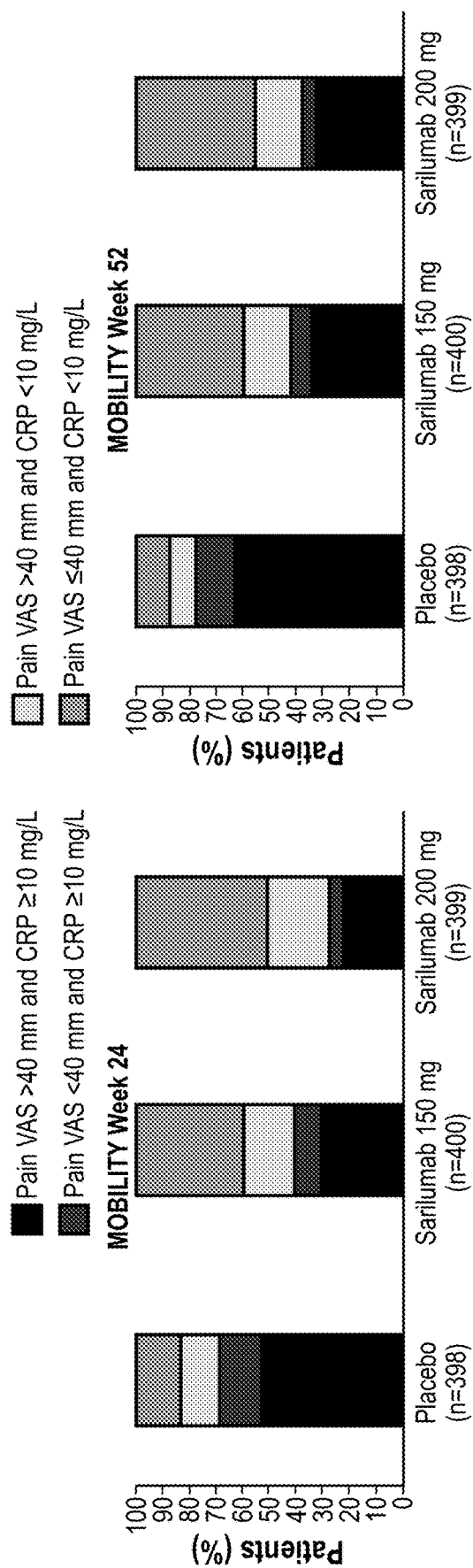

This disclosure provides pharmaceutical compositions and methods of using these compositions for the treatment of unacceptable pain (UP) levels. In some embodiments, the UP persists despite inflammation control (IC). In some embodiments, the IC is biologic treatment induced. These compositions and methods include at least one antibody that specifically binds interleukin-6 receptor (hIL-6R).

As used within the Claims, the Summary, and the Detailed Description herein, the term "about" in quantitative terms refers to plus or minus 10% of the value it modifies (rounded up to the nearest whole number if the value is not subdividable, such as a number of molecules or nucleotides). For example, the phrase "about 100 mg" would encompass 90 mg to 110 mg, inclusive; the phrase "about 2500 mg" would encompass 2250 mg to 2750 mg. When applied to a percentage, the term "about" refers to plus or minus 10% relative to that percentage. For example, the phrase "about 20%" would encompass 18-22% and "about 80%" would encompass 72-88%, inclusive. Moreover, where "about" is used herein in conjunction with a quantitative term it is understood that in addition to the value plus or minus 10%, the exact value of the quantitative term is also contemplated and described. For example, the term "about 23%" expressly contemplates, describes, and includes exactly 23%.

It is to be noted that the term "a" or "an" entity refers to one or more of that entity; for example, "a symptom," is understood to represent one or more symptoms. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

The term "pain" refers to discomfort caused by intense or damaging stimuli including illness, injury, or mental anguish. In some embodiments, pain has both physical and emotional components and it is experienced as an unpleasant sensation that can range from mild, localized discomfort to agony.

The term "unacceptable pain" refers to a level indicated by a patient acceptable symptom state (PASS), a validated measure that indicates the level of acceptable pain. PASS uses a threshold of 40 mm on a visual analog scale (VAS) that ranges from 0-100 mm, meaning that VAS>40 mm indicates unacceptable pain. See Lourdudoss et al. (Dietary intake of polyunsaturated fatty acids and pain in spite of inflammatory control among methotrexate-treated early rheumatoid arthritis patients. Arthritis Care and Research. 2018; 70(2):205-212); and Pham and Tubach (Patient acceptable symptomatic state (PASS). Joint Bone Spine 2009; 76:321-3), which are each incorporated herein by reference in their entireties. In some embodiments, pain experienced in the previous week is measured. In some embodiments, pain experienced in the previous 2, 3, 4, 5, 6, 7, 8 or more weeks is measured. In some embodiments, pain experienced in the previous month is measured. In some embodiments, pain experienced in the previous, 2, 3, 4, 5, 6, 7, 8, 9, 10, 11, 12 or more months is measured. In some embodiments, pain experienced in the previous year is measured. In some embodiments, pain experienced for the previous 2, 3, 4, 5, 6, 7, 8, 9, 10 or more years is measured.

A subject experiencing "refractory pain" has rheumatoid arthritis, unacceptable pain, and a serum level of C-reactive protein (CRP) of <10 mg/L. A subject experiencing "strict refractory pain" has rheumatoid arthritis, unacceptable pain, a swollen joint count (SJC) of less than or equal to 1, and a serum level of CRP<10 mg/L. In some embodiments, the rheumatoid arthritis is moderately-to-severe active rheumatoid arthritis.

IL-6 interacts directly with the IL-6Rα subunit and the IL-6/IL-6Rα pair forms a high affinity complex with the glycoprotein 130 (gp130) subunit. IL-6Rα also exists in a soluble form, which is involved in trans-signaling and allows IL-6 to affect cells that do not express IL-6Rα including synovial cells in the joint (Rose-John et al., J Leukoc Biol. 2006; 80(2), 227-36). Sarilumab (SAR153191), also designated as REGN88, is a recombinant IgG1 kappa monoclonal antibody of fully human sequence directed against the alpha subunit of the IL-6 receptor complex (IL-6Rα). Sarilumab is a potent and specific inhibitor of IL-6 signaling. By binding to IL-6Rα with high affinity, sarilumab blocks the binding of IL-6 and interrupts the cytokine-mediated signaling cascade. In certain embodiments, interleukin-6 is a key element in the etiology of rheumatic conditions and inhibition of its signaling is a critical part of the mechanism of action of sarilumab. In ex vivo assays, sarilumab did not demonstrate antibody-dependent cellular cytotoxicity (ADCC) or complement-dependent cytotoxicity (CDC) on relevant cell types where sarilumab binding was verified by fluorescenceactivated cell sorter (FACS) analysis (Committee for Medicinal Products for Human Use, Assessment Report, Apr. 27, 2017 EMA/292840/2017, available at www_dot_ema_dot_europa_dot_eu/documents/assessment_report/kevzara_epar_public_assessment_report_en_dot_pdf.

Antibodies

The present disclosure includes methods that comprise administering to a subject an antibody, or an antigen-binding fragment thereof, that binds specifically to hIL-6R. As used herein, the term "hIL-6R" means a human cytokine receptor that specifically binds human interleukin-6 (IL-6). In certain embodiments, the antibody that is administered to the patient binds specifically to the extracellular domain of hIL-6R.

The term "antibody", as used herein, refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In some embodiments, the FRs of the antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, and bivalent nanobodies), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may in various embodiments consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody may in various embodiments comprise a homo-dimer or hetero-dimer (or other multimer) of any of the variable and constant domain configurations listed above in non-covalent association with one another and/or with one or more monomeric VH or VL domain (e.g., by disulfide bond(s)).

In certain embodiments, the antibody or antibody fragment for use in a method disclosed herein may be a monospecific antibody. In certain embodiments, the antibody or antibody fragment for use in a method disclosed herein may be a multispecific antibody, which may be specific for different epitopes of one target polypeptide or may contain antigen-binding domains specific for epitopes of more than one target polypeptide. An exemplary bi-specific antibody format that can be used in the context certain embodiments involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise an Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of certain embodiments. Any multispecific antibody format, including the exemplary bispecific antibody formats disclosed herein, may in various embodiments be adapted for use in the context of an antigen-binding fragment of an anti-IL-6R antibody using routine techniques available in the art.

The fully-human anti-IL-6R antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s) (such sequence changes are referred to herein as "germline back-mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework residues and/or CDR residues within the VH and/or VL domains are mutated back to the germline sequence. In other embodiments, only certain residues are mutated back to the germline sequence, e.g., only the mutated residues found within the first 8 amino acids of FR1 or within the last 8 amino acids of FR4, or only the mutated residues found within CDR1, CDR2 or CDR3. Furthermore, included herein are antibodies that may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity. The term "human antibody", as used herein, is intended to include antibodies having variable and constant regions derived from human germline immunoglobulin sequences. The human antibodies featured in the disclosure may in various embodiments nonetheless include amino acid residues not encoded by human germline immunoglobulin sequences (e.g., mutations introduced by random or site-specific mutagenesis in vitro or by somatic mutation in vivo), for example in the CDRs and in some embodiments CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al., (1992) Nucl. Acids Res. 20:6287-6295, incorporated herein by reference in its entirety) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Human antibodies can exist in two forms that are associated with hinge heterogeneity. In an embodiment, an immunoglobulin molecule comprises a stable four chain construct of approximately 150-160 kDa in which the dimers are held together by an interchain heavy chain disulfide bond. In another embodiment, the dimers are not linked via inter-chain disulfide bonds and a molecule of about 75-80 kDa is formed composed of a covalently coupled light and heavy chain (half-antibody). In certain embodiments, these forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al., (1993) Molecular Immunology 30:105, incorporated by reference in its entirety) to levels typically observed using a human IgG1 hinge. The instant disclosure encompasses in various embodiments antibodies having one or more mutations in the hinge, CH2 or CH3 region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody." In various embodiments, the isolated antibody also includes an antibody in situ within a recombinant cell. In other embodiments, isolated antibodies are antibodies that have been subjected to at least one purification or isolation step. In various embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-6R, as used herein, includes antibodies that bind IL-6R (e.g., human IL-6R) or portion thereof with a KD of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or about 0.5 nM, as measured in a surface plasmon resonance assay. In some embodiments, the antibody binds IL-6R (e.g., human IL-6Rα) with a KD of from about 0.1 nM to about 1000 nM or from about 1 nM to about 100 nM. In some embodiments, the antibody binds IL-6R (e.g., human IL-6Rα) with a KD of from about 1 pM to about 100 pM or from about 40 pM to about 60 pM. Specific binding can also be characterized by a dissociation constant of at least about $1 \times 10^{-6}$ M or smaller. In other embodiments, the dissociation constant is at least about $1 \times 10^{-7}$ M, $1 \times 10^{-8}$ M, or $1 \times 10^{-9}$ M. An isolated antibody that specifically binds human IL-6R may, however, have cross-reactivity to other antigens, such as IL-6R molecules from other (non-human) species.

The term "surface plasmon resonance", as used herein, refers to an optical phenomenon that allows for the analysis of real-time interactions by detection of alterations in protein concentrations within a biosensor matrix, for example using the BIACORE system (Biacore Life Sciences division of GE Healthcare, Piscataway, NJ).

The term "KD", as used herein, is intended to refer to the equilibrium dissociation constant of an antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The anti-IL-6R antibodies useful for the methods described herein may in various embodiments include one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes in various embodiments methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). Numerous antibodies and antigen-binding fragments may be constructed which comprise one or more individual germline mutations or combinations thereof. In certain embodiments, all of the framework and/or CDR residues within the VH and/or VL domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies may contain any combination of two or more germline mutations within the framework and/or CDR regions, e.g., wherein certain individual residues are mutated to the corresponding residue of a certain germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present disclosure.

The present disclosure also includes methods involving the use of anti-IL-6R antibodies comprising variants of any of the HCVR, LCVR, and/or CDR amino acid sequences disclosed herein having one or more conservative substitutions. For example, the present disclosure includes the use of anti-IL-6R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

According to the present disclosure, the anti-IL-6R antibody, or antigen-binding fragment thereof, in various embodiments comprises a heavy chain variable region (HCVR), light chain variable region (LCVR), and/or complementarity determining regions (CDRs) comprising any of the amino acid sequences of the anti-IL-6R antibodies described in U.S. Pat. No. 7,582,298, incorporated herein by reference in its entirety. In certain embodiments, the anti-IL-6R antibody or antigen-binding fragment thereof comprises the heavy chain complementarity determining regions (HCDRs) of a HCVR comprising the amino acid sequence of SEQ ID NO: 1 and the light chain complementarity determining regions (LCDRs) of a LCVR comprising the amino acid sequence of SEQ ID NO: 2. According to certain embodiments, the anti-IL-6R antibody or antigen-binding fragment thereof comprises three HCDRs (i.e., HCDR1, HCDR2 and HCDR3) and three LCDRs (i.e., LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In yet other embodiments, the anti-IL-6R antibody or antigen-binding fragment thereof comprises an HCVR comprising the amino acid sequence of SEQ ID NO: 1 and an LCVR comprising the amino acid sequence of SEQ ID NO: 2.

In another embodiment, the anti-IL-6R antibody or antigen-binding fragment thereof comprises a heavy chain comprising the amino acid sequence of SEQ ID NO: 9 and a light chain comprising the amino acid sequence of SEQ ID NO: 10. In some embodiments, the extracellular domain of hIL-6R comprises the amino acid sequence of SEQ ID NO: 11. According to certain exemplary embodiments, the methods of the present disclosure comprise the use of the anti-IL-6R antibody referred to and known in the art as sarilumab, or a bioequivalent thereof.

```
The amino acid sequence of SEQ ID NO: 1 is
EVQLVESGGGLVQPGRSLRLSCAASRFTFDDYAMHWVRQAPGKGLEWVSGI

SWNSGRIGYADSVKGRFTISRDNAENSLFLQMNGLRAEDTALYYCAKGRDS

FDIWGQGTMVTVSS.

The amino acid sequence of SEQ ID NO: 2 is
DIQMTQSPSSVSASVGDRVTITCRASQGISSWLAWYQQKPGKAPKLLIYGA

SSLESGVPSRFSGSGSGTDFTLTISSLQPEDFASYYCQQANSFPYTFGQGT

KLEIK.

The amino acid sequence of SEQ ID NO: 3 is
RFTFDDYA.

The amino acid sequence of SEQ ID NO: 4 is
ISWNSGRI.

The amino acid sequence of SEQ ID NO: 5 is
AKGRDSFDI.

The amino acid sequence of SEQ ID NO: 6 is
QGISSW.

The amino acid sequence of SEQ ID NO: 7 is
GAS.

The amino acid sequence of SEQ ID NO: 8 is
QQANSFPYT.

The amino acid sequence of SEQ ID NO: 9 is
EVQLVESGGGLVQPGRSLRLSCAAS<u>RFTFDDYA</u>MHWVRQAPGKGLEWVSGI SWNS<u>GRIGYA</u>DSVKGRFTISRDNAENSLFLQMNGLRAEDTALYYC<u>AKGRDS</u>

<u>FDI</u>WGQGTMVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRT

PEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSK

LTVDKSRWQQGNVFSCSVMHEALHNHYTQKSLSLSPGK.

The amino acid sequence of SEQ ID NO: 10 is
DIQMTQSPSSVSASVGDRVTITCRASQGISSWLAWYQQKPGKAPKLLIYGA

SSLESGVPSRFSGSGSGTDFTLTISSLQPEDFASYYCQQANSFPYTFGQGT

KLEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.

The sequence of SEQ ID NO: 11 is
MVAVGCALLAALLAAPGAALAPRRCPAQEVARGVLTSLPGDSVTLTCPGVE

PEDNATVHWVLRKPAAGSHPSRWAGMGRRLLLRSVQLHDSGNYSCYRAGRP

AGTVHLLVDVPPEEPQLSCFRKSPLSNVVCEWGPRSTPSLTTKAVLLVRKF

QNSPAEDFQEPCQYSQESQKFSCQLAVPEGDSSFYIVSMCVASSVGSKFSK

TQTFQGCGILQPDPPANITVTAVARNPRWLSVTWQDPHSWNSSFYRLRFEL

RYRAERSKTFTTWMVKDLQHHCVIHDAWSGLRHVVQLRAQEEFGQGEWSEW

SPEAMGTPWTESRSPPAENEVSTPMQALTTNKDDDNILFRDSANATSLPVQ

D.
```

The term "bioequivalent" as used herein, refers to a molecule having similar bioavailability (rate and extent of availability) after administration at the same molar dose and under similar conditions (e.g., same route of administration), such that the effect, with respect to both efficacy and safety, can be expected to be essentially same as the comparator molecule. Two pharmaceutical compositions comprising an anti-IL-6R antibody are bioequivalent if they are pharmaceutically equivalent, meaning they contain the same amount of active ingredient (e.g., IL-6R antibody), in the same dosage form, for the same route of administration and meeting the same or comparable standards. Bioequivalence can be determined, for example, by an in vivo study comparing a pharmacokinetic parameter for the two compositions. Parameters commonly used in bioequivalence studies include peak plasma concentration (Cmax) and area under the plasma drug concentration time curve (AUC).

The disclosure in certain embodiments relates to methods comprising administering to the subject an antibody which comprises the heavy chain variable region comprising sequence SEQ ID NO: 1 and the light chain variable region comprising sequence SEQ ID NO: 2.

The disclosure provides pharmaceutical compositions comprising such antibody, and methods of using these compositions.

The antibody in various embodiments comprises the heavy chain variable region comprising sequence SEQ ID NO: 1 and the light chain variable region comprising sequence SEQ ID NO: 2 is an antibody that specifically binds human interleukin-6 receptor (hIL-6R). See international publication number WO2007/143168, incorporated herein by reference in its entirety. In one embodiment, the antibody comprises the heavy chain variable region comprising sequence SEQ ID NO: 9 and the light chain variable region comprising sequence SEQ ID NO: 10. In various embodiments, the antibody is sarilumab.

DMARDs

Disease-modifying antirheumatic drugs (DMARDs) are drugs defined by their use in rheumatoid arthritis to slow down disease progression. DMARDs have been classified as synthetic (sDMARD) and biological (bDMARD). Synthetic DMARDs include non-exhaustively methotrexate, sulfasalazine, leflunomide, and hydroxychloroquine. Biological DMARDs include non-exhaustively adalimumab, golimumab, etanercept, abatacept, infliximab, rituximab, and tocilizumab. In some embodiments, the DMARD is a TNF antagonist. TNF antagonists include etanercept, infliximab, adalimumab, golimumab and certolizumab pegol.

Methods of Administration and Formulations

The methods described herein comprise administering a therapeutically effective amount of an anti-IL-6R antibody to a subject. As used herein, an "effective amount" or "therapeutically effective amount" is a dose of the therapeutic that results in treatment of unacceptable pain (UP). In certain embodiments, effective amount is a dose of the therapeutic that results in treatment of UP that persists despite inflammation control (IC). As used herein, "treating" refers to causing a detectable improvement in one or more symptoms associated with UP or causing a biological effect (e.g., a decrease in the level of a particular biomarker) that is correlated with the underlying pathologic mechanism(s) giving rise to the condition or symptom(s). For example, a dose of anti-IL-6R antibody which causes a reduction in UP is deemed a "therapeutically effective amount."

An "improvement" in a pain-associated symptom in various embodiments refers reduction in the incidence of the pain symptom which may correlate with an improvement in one or more pain-associated tests, scores or metrics (as described herein). For example, the improvement may correlate a decrease from baseline of one or more of pain criteria. In various embodiments, improvement may comprise a decrease in VAS from baseline. In various embodiments, the baseline score of VAS is ≥40 mm and is reduced to a score ≤40 mm. As used herein, the term "baseline," with regard to a pain-associated parameter, means the numerical value of the pain-associated parameter for a patient prior to or at the time of administration of the antibody of the present invention. A detectable "improvement" can also be detected using at least one test, score or metric described herein. In various embodiments, the improvement is detected using VAS. In various embodiments, the improvement is characterized by its relation to a subject's PASS status.

In various embodiments, previous treatment with a DMARD other than an anti-IL-6R antibody (such as sarilumab) has been inadequate (e.g., as assessed by the subject and/or a physician), has been ineffective and/or has not resulted in a detectable improvement in one or more parameters or symptoms associated with pain and/or has not caused a biological effect that is correlated with the underlying pathologic mechanism(s) giving rise to the condition or symptom(s) of pain.

In various embodiments, a IL-6R antibody is administered subcutaneously. In various embodiments, the IL-6R antibody is sarilumab.

In various embodiments, a therapeutically effective amount of anti-IL-6R antibody that is administered to the subject will vary depending upon the age and the size (e.g., body weight or body surface area) of the subject as well as the route of administration and other factors well known to those of ordinary skill in the art.

In various embodiments, the dose is a fixed dose regardless of the body weight or surface area of the subject. In various embodiments, the subject is at least 18 years old. In various embodiments, the subject is from 30 to 100 years old. In various embodiments, the subject is from 35 to 100 years old. In various embodiments, the subject is from 35 to 8 years old. In various embodiments, the subject is from 40 to 70 years old.

The disclosure provides methods of using therapeutic compositions comprising anti-IL-6R antibodies or antigen-binding fragments thereof and, optionally, one or more additional therapeutic agents. The therapeutic compositions of the invention will be administered with suitable carriers, excipients, and/or other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA, incorporated herein by reference in its entirety. These formulations include, for example, powders, pastes, ointments, jellies, waxes, oils, lipids, lipid (cationic or anionic) containing vesicles (such as LIPOFECTIN), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311, incorporated herein by reference in its entirety.

Various delivery systems are known and can be used to administer pharmaceutical compositions provided herein, e.g., encapsulation in liposomes, microparticles, microcapsules, receptor mediated endocytosis (see, e.g., Wu et al. (1987) J. Biol. Chem. 262:4429-4432, incorporated herein by reference in its entirety). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The IL-6R antibody can be administered subcutaneously.

The pharmaceutical composition can also be delivered in a vesicle, such as a liposome (see Langer (1990) Science 249:1527-1533, incorporated herein by reference in its entirety). In certain embodiments, the pharmaceutical composition can be delivered in a controlled release system, for example, with the use of a pump or polymeric materials. In certain embodiments, a controlled release system can be placed in proximity of the composition's target, thus requiring only a fraction of the systemic dose.

The injectable preparations may include dosage forms for intravenous, subcutaneous, intracutaneous and intramuscular injections, local injection, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc.). As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

The antibody is typically formulated as described herein and in international publication number WO2011/085158, incorporated herein by reference in its entirety.

In various embodiments, the antibody is administered as an aqueous buffered solution at about pH 6.0 containing
about 21 mM histidine,
about 45 mM arginine,
about 0.2% (w/v) polysorbate 20,
about 5% (w/v) sucrose, and
between about 100 mg/mL and about 200 mg/mL of the antibody.

In another embodiment, the antibody is administered as an aqueous buffered solution at about pH 6.0 containing
about 21 mM histidine,
about 45 mM arginine,
about 0.2% (w/v) polysorbate 20,
about 5% (w/v) sucrose, and
at least about 130 mg/mL of the antibody.

In another embodiment, the antibody is administered as an aqueous buffered solution at about pH 6.0 containing
about 21 mM histidine,
about 45 mM arginine,
about 0.2% (w/v) polysorbate 20,
about 5% (w/v) sucrose, and
about 131.6 mg/mL of the antibody.

In another embodiment, the antibody is administered as an aqueous buffered solution at about pH 6.0 containing
about 21 mM histidine,
about 45 mM arginine,
about 0.2% (w/v) polysorbate 20,
about 5% (w/v) sucrose; and
about 175 mg/mL of the antibody.

In other embodiments, the antibody is administered as an aqueous buffered solution at pH 6.0 containing
21 mM histidine,
45 mM arginine,
0.2% (w/v) polysorbate 20,
5% (w/v) sucrose, and
between 100 mg/mL and 200 mg/mL of the antibody.

In another embodiment, the antibody is administered as an aqueous buffered solution at pH 6.0 containing
21 mM histidine,
45 mM arginine,
0.2% (w/v) polysorbate 20,
5% (w/v) sucrose, and
at least 130 mg/mL of the antibody.

In another embodiment, the antibody is administered as an aqueous buffered solution at pH 6.0 containing
21 mM histidine,
45 mM arginine,
0.2% (w/v) polysorbate 20,
5% (w/v) sucrose, and
131.6 mg/mL of the antibody.

In another embodiment, the antibody is administered as an aqueous buffered solution at pH 6.0 containing
21 mM histidine,
45 mM arginine,
0.2% (w/v) polysorbate 20,
5% (w/v) sucrose; and
175 mg/mL of the antibody.

In various embodiments, the antibody is administered in a stable pharmaceutical formulation comprising: (i) histidine at a concentration of from 25 mM to 100 mM; (ii) arginine at a concentration of from 25 mM to 50 mM; (iii) sucrose in an amount of from 3% to 10% w/v; and (iv) polysorbate 20 in an amount of from 0.1% to 0.2%, wherein the formulation has a pH of about 5.8, about 6.0, or about 6.2, and at least 90% of the native form of the antibody is recovered after 1 month of storage at 45° C., as determined by size exclusion chromatography. In various embodiments, about 150 mg of the antibody (e.g., sarilumab) is administered to the subject.

In various embodiments, the antibody is administered in a stable pharmaceutical formulation comprising: (i) histidine at a concentration of from about 10 mM to about 25 mM; (ii) arginine at a concentration of from about 25 mM to about 50 mM; (iii) sucrose in an amount of from about 5% to about 10% w/v; and (iv) polysorbate in an amount of from about 0.1% to about 0.2% w/v, wherein the formulation has a pH of about 5.8, about 6.0, or about 6.2, and at least 90% of the native form of the antibody is recovered after 1 month of storage at 45° C., as determined by size exclusion chromatography. In various embodiments, about 150 mg of the antibody (e.g., sarilumab) is administered to the subject.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

In various embodiments, the anti-IL-6R antibody (or pharmaceutical formulation comprising the antibody) can be administered to the patient using any acceptable device or mechanism. For example, the administration can be accomplished using a syringe and needle or with a reusable pen and/or autoinjector delivery device. The methods of the present disclosure include the use of numerous reusable pen and/or autoinjector delivery devices to administer an anti-IL-6R antibody (or pharmaceutical formulation comprising the antibody). Examples of such devices include, but are not limited to AUTOPEN (Owen Mumford, Inc., Woodstock, UK), DISETRONIC pen (Disetronic Medical Systems, Bergdorf, Switzerland), HUMALOG MIX 75/25 pen, HUMALOG pen, HUMALIN 70/30 pen (Eli Lilly and Co., Indianapolis, IN), NOVOPEN I, II and III (Novo Nordisk, Copenhagen, Denmark), NOVOPEN JUNIOR (Novo Nordisk, Copenhagen, Denmark), BD pen (Becton Dickinson, Franklin Lakes, NJ), OPTIPEN, OPTIPEN PRO, OPTIPEN STARLET, and OPTICLIK (Sanofi-Aventis, Frankfurt, Germany). Examples of disposable pen and/or autoinjector delivery devices having applications in subcutaneous delivery of a pharmaceutical composition of the present disclosure include, but are not limited to the SOLOSTAR pen (Sanofi-Aventis), the FLEXPEN (Novo Nordisk), and the KWIKPEN (Eli Lilly), the SURECLICK Autoinjector (Amgen, Thousand Oaks, CA), the PENLET (Haselmeier, Stuttgart, Germany), the EPIPEN (Dey, L. P.), and the HUMIRA Pen (AbbVie Inc., North Chicago, IL), to name only a few.

In various embodiments, the antibody is administered with a prefilled syringe. In various embodiments, the antibody is administered with a prefilled syringe containing a safety system. For example, the safety system prevents an accidental needle-stick injury. In various embodiments, the antibody is administered with a prefilled syringe containing an ERIS safety system (West Pharmaceutical Services Inc.). See also U.S. Pat. Nos. 5,215,534 and 9,248,242, incorporated herein by reference in their entireties.

In various embodiments, the antibody is administered with an auto-injector. In various embodiments, the antibody is administered with an auto-injector featuring the PUSH-CLICK technology (SHL Group). In various embodiments, the auto-injector is a device comprising a syringe that allows for administration of a dose of the composition and/or antibody to a subject. See also U.S. Pat. Nos. 9,427,531 and 9,566,395, incorporated herein by reference in their entireties.

The use of a microinfusor to deliver an anti-IL-6R antibody (or pharmaceutical formulation comprising the antibody) to a patient is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., J. Controlled Release 46:107-116 (1996), incorporated herein by reference in their entireties. Microinfusors are particularly useful for the delivery of large doses of therapeutic proteins contained within high concentration (e.g., about 100, 125, 150, 175, 200 mg/mL or more) and/or viscous solutions.

In various embodiments, an inadequate response to prior treatment refers to subjects whose pain is not well controlled after receiving the prior treatment at the maximum tolerated typical dose. In an embodiment, an inadequate response to prior treatment refers to subjects who have moderate or high disease activity and features of poor prognosis despite prior treatment. In various embodiments, an inadequate response to prior treatment refers to subjects with a pain symptom (e.g., any symptom listed herein) that has not improved or that has worsened despite prior treatment.

Patient Population

As used herein, "subject" means a human subject or human patient.

An antibody as described herein is in various embodiments administered to subjects who have rheumatoid arthritis and are suffering from unacceptable pain (UP), UP in subjects with inflammation control (IC) or UP in subjects with strict RP. In various embodiments, the subject has UP and rheumatoid arthritis. In various embodiments, the subject has UP-IC and rheumatoid arthritis. In various embodiments, the subject has UP strict RP and rheumatoid arthritis. In various embodiments, the subject was previously ineffectively treated for rheumatoid arthritis by administering one or more DMARDs different from the IL-6R antibody.

A subject who is considered "ineffectively treated" by his or her physician is a subject who in various embodiments either has shown to be intolerant to the one or more DMARDs tested by the physician, and/or a subject who has shown an inadequate response to the one or more DMARDs tested by the physician, typically a subject who is still considered by the physician to present with, or to have, UP despite the previous one or more DMARDs administered.

In various embodiments, a subject with rheumatoid arthritis has:
  at least 6 of 66 swollen joints and 8 of 68 tender joints, as counted by the physician in a typical quantitative swollen and tender joint count examination,
  High sensitivity C-reactive protein (hs-CRP)≥8 mg/L or ESR≥28 mm/H
  DAS28ESR>5.1.

In various embodiments, the subject, who was previously ineffectively treated for rheumatoid arthritis by administering at least one DMARD different from the antibody, is a subject who was previously ineffectively treated for UP by administering a DMARD. In various embodiments, the DMARD is selected from the group consisting of methotrexate, sulfasalazine, leflunomide, and hydroxychloroquine. In various embodiments, the DMARD is methotrexate. In various embodiments, the DMARD is a TNF-α antagonist. In various embodiments, the DMARD is adalimumab.

In various embodiments, the subject, who was previously ineffectively treated for UP by administering one or more DMARD different from the antibody, is a subject who had an inadequate response or intolerance to methotrexate.

In various embodiments, for those subjects previously ineffectively treated for UP by administering one or more DMARD different from the IL-6R antibody, the one or more DMARD is/are not administered anymore to the subject, and the IL-6R antibody is in various embodiments administered alone, in monotherapy to the subject.

In various embodiments, the subject is intolerant to the DMARD due to one or more physical reactions, conditions or symptoms from the treatment with the DMARD. Physical reactions, conditions or symptoms can include allergies, pain, nausea, diarrhea, azotemia, bleeding of the stomach, intestinal bleeding, canker sores, decreased blood platelets, perforation of the intestine, bacterial infection, inflammation of gums or mouth, inflammation of the stomach lining or intestinal lining, bacterial sepsis, stomach ulcer, intestinal ulcer, sun sensitive skin, dizziness, loss of appetite, low energy, and vomiting. In certain embodiments, intolerance can be determined by the subject or by a medical professional upon examination of the subject. In various embodiments, the DMARD is selected from the group consisting of methotrexate, sulfasalazine, leflunomide, and hydroxychloroquine. In certain embodiments, the DMARD is methotrexate.

In certain embodiments the disclosure provides administering to the subject one or more additional therapeutic agents in combination with the IL-6R antibody. As used herein, the expression "in combination with" means that the additional therapeutic agents are administered before, after, or concurrent with the pharmaceutical composition comprising the IL-6R antibody. In certain embodiments, the subject is administered the antibody with a DMARD and/or TNF-α antagonist.

All publications mentioned herein are incorporated herein by reference in their entirety for all purposes.

EXAMPLE

Example 1: Odds Ratios for Unacceptable Pain (UP) and Unacceptable Pain Despite Refractory Pain (RC) or Inflammation Control-Strict (RP-Strict) for Three Randomized Controlled Clinical Trials (RCTs) of Sarilumab It has been previously observed in three RCTs of sarilumab given subcutaneously at a dose of 150 mg or 200 mg every 2 weeks versus other treatments that sarilumab improved pain in RA patients.

Across all three trials (with similar baseline characteristics per arm in each trial, see Table 1), sarilumab administered at 150 mg and 200 mg was associated with better inflammation control and lower rates of UP versus comparators (see FIGS. 2A-2C) and had lower odds of UP versus comparators (nominal p<0.05, See FIG. 1A-1C).

Across all three RCTs, sarilumab 150 mg and 200 mg had lower odds of unacceptable pain versus comparators with ORs (FIG. 1A):
  MOBILITY, Week 24 sarilumab 150 mg: 0.46 [0.34, 0.61]; sarilumab 200 mg: 0.39 [0.29, 0.52]) and MOBILITY, Week 52 (sarilumab 150 mg: 0.40 [0.30, 0.54]; sarilumab 200 mg: 0.39 [0.30, 0.53]; all nominal p<0.001
  TARGET, sarilumab 150 mg: 0.41 [0.26, 0.65]; sarilumab 200 mg: 0.44 [0.28, 0.69]); nominal p<0.05

MONARCH, sarilumab 200 mg: 0.54 [0.36, 0.81]; nominal p<0.05

Data from the MOBILITY trial showed both sarilumab doses had lower odds (nominal p<0.05) of RP despite inflammation control when compared to placebo at Week 24 (sarilumab 150 mg: 0.60 [0.38, 0.93]; sarilumab 200 mg: 0.57 [0.37, 0.87]) and Week 52 (sarilumab 150 mg: 0.64 [0.37, 1.02]; sarilumab 200 mg: 0.62 [0.37, 1.02]), and RP-strict (MOBILITY trial) at Week 52 (sarilumab 150 mg: 0.41 [0.19, 0.90]; sarilumab 200 mg: 0.35 [0.16, 0.76]) (FIG. 1C). Data from the TARGET trial showed that sarilumab at 150 mg had lower odds (p<0.05) of RP-strict at Week 24 (0.05 [0.01; 0.39]). Higher pain level was associated with worse level of FACIT-fatigue, HAQ, SJC and TJC (all p<0.001), and UP had mostly moderate agreements with the likelihood of achieving response on minimal clinically important differences on all these outcomes (Kappa coefficient values 0.41-0.60).

There were no significant differences in the odds of refractory pain for sarilumab 200 mg versus placebo or adalimumab 40 mg in TARGET and MONARCH, respectively.

Overall Study Design and Plan:
Post Hoc Analysis of Three Randomized Controlled Clinical Trials (RCTs)

Data from three Phase 3 RCTs were collected to determine if sarilumab contributed to improvements in pain in subjects with RA. The MOBILITY study [NCT01061736] administered 150 mg or 200 mg sarilumab with conventional DMARDs in patients once every two weeks compare to placebo for 24 or 52 weeks; the TARGET study [NCT01709578] administered sarilumab with conventional DMARDs in patients for 24-weeks; and the MONARCH study [NCT02332590] compared patients given 200 mg sarilumab monotherapy once every two weeks to patients that received 40 mg adalimumab monotherapy once every two weeks. Post-hoc analyses were conducted on the odds rations (ORs) of pain outcomes: UP (based on patient acceptable symptom state [PASS] on a threshold of Visual Analog Scale pain >40 mm [0-100]), RP (UP C-reactive protein <10 mg/L and RP-strict (RP with swollen joint count ≤1), and associations between pain and fatigue (FACIT-Fatigue) and disease activity (Health Assessment Questionnaire [HAQ], SJC, and tender joint count [TJC]). The demographics and clinical characteristics of the populations for each trial are outlined in Table 1.

TABLE 1

Demographics and clinical characteristics of trial population

MOBILITY Trial

|  | Placebo + methotrexate (n = 398) | 150 mg q2w + methotrexate (n = 400) | 200 mg q2w + methotrexate (n = 399) |
| --- | --- | --- | --- |
| Age, years, mean ± SD | 50.9 ± 11.2 | 50.1 ± 11.9 | 50.8 ± 11.8 |
| Female, n (%) | 321 (80.7) | 319 (79.8) | 337 (84.9) |
| Race, White - Caucasian, n (%) | 343 (86.2) | 345 (86.3) | 343 (86.0) |
| Duration of RA, years, mean ± SD | 9.1 ± 8.1 | 9.5 ± 8.5 | 8.6 ± 7.0 |
| CRP, mean ± SD | 20.5 ± 23.0 | 22.5 ± 23.1 | 22.2 ± 23.8 |
| SJC (66 assessed), mean ± SD | 16.7 ± 9.3 | 16.6 ± 9.0 | 16.8 ± 9.7 |
| TJC, mean ± SD | 26.8 ± 13.7 | 27.2 ± 14.2 | 26.5 ± 14.5 |
| Pain-VAS, mean ± SD | 63.7 ± 19.9 | 65.5 ± 21.4 | 66.7 ± 21.4 |
| HAQ-DI, mean ± SD | 1.6 ± 0.7 | 1.6 ± 0.6 | 1.7 ± 0.6 |
| FACIT-Fatigue, mean ± SD | 27.2 ± 10.4 | 26.3 ± 9.8 | 25.9 ± 10.4 |

TARGET Trial

|  | Placebo + csDMARD(s) (n = 181) | 150 mg q2w + csDMARD(s) (n = 181) | 200 mg q2w + csDMARD(s) (n = 184) |
| --- | --- | --- | --- |
| Age, years, mean ± SD | 51.9 ± 12.4 | 54.0 ± 11.7 | 52.9 ± 12.9 |
| Female, n (%) | 154 (85.1) | 142 (78.5) | 151 (82.1) |
| Race, White - Caucasian, n (%) | 124 (68.5) | 134 (74.0) | 130 (70.7) |
| Duration of RA, years, mean ± SD | 12.0 ± 10.0 | 11.6 ± 8.6 | 12.7 ± 96 |
| CRP, mean ± SD | 26.0 ± 25.2 | 23.6 ± 23.4 | 30.8 ± 28.4 |
| SJC (66 assessed), mean ± SD | 20.2 ± 11.3 | 19.6 ± 11.2 | 20.0 ± 11.9 |
| TJC, mean ± SD | 29.4 ± 14.5 | 27.7 ± 15.6 | 29.6 ± 15.5 |
| Pain-VAS, mean ± SD | 71.6 ± 18.2 | 71.0 ± 19.4 | 74.9 ± 18.4 |
| HAQ-DI, mean ± SD | 1.8 ± 0.6 | 1.7 ± 0.6 | 1.8 ± 0.6 |
| FACIT-Fatigue, mean ± SD | 23.7 ± 10.8 | 23.5 ± 10.6 | 23.1 ± 10.8 |

MONARCH Trial

|  | Adalimumab SC 40 mg q2w/qw (n = 185) | Sarilumab SC 200 mg q2w (n = 184) |
| --- | --- | --- |
| Age, years, mean ± SD | 53.6 ± 11.9 | 50 ± 12.6 |
| Female, n (%) | 150 (81.1) | 157 (85.3) |
| Race, White - Caucasian, n (%) | 164 (88.6) | 171 (92.9) |
| Duration of RA, years, mean ± SD | 6.6 ±7.8 | 8.1 ± 8.1 |
| CRP, mean ± SD | 24.1 ± 31.0 | 17.4 ± 21.3 |
| SJC (66 assessed), mean ± SD | 17.5 ± 10.3 | 18.6 ± 10.7 |

TABLE 1-continued

| Demographics and clinical characteristics of trial population | | |
|---|---|---|
| TJC, mean ± SD | 26.7 ± 13.6 | 28.0 ± 13.2 |
| Pain-VAS, mean ± SD | 71.4 ± 18.96 | 71.6 ± 18.65 |
| HAQ-DI, mean ± SD | 1.6 ± 0.64 | 1.6 ± 0.55 |
| FACIT-Fatigue, mean ± SD | 24.0 ± 10.31 | 23.6 ± 9.01 |

Abbreviations:
qw = once every week;
q2w = once every other week;
SC = subcutaneous;
HAQ-DI = Health Assessment Questionnaire Disability Index;
SD = Standard Deviation

The invention claimed is:

1. A method for treating unacceptable pain (UP) in a subject in need thereof who has rheumatoid arthritis, comprising:
administering to a subject who is determined to have rheumatoid arthritis, UP despite inflammation control, and a serum level of C-reactive protein (CRP) of less than 10 mg/L, wherein the UP has a level of pain indicated by a visual analog scale (VAS) of greater than 40 mm, a therapeutically effective dose of an antibody that specifically binds to an IL-6 receptor, wherein the antibody comprises a heavy chain variable region comprising complementarity determining regions HCDR1, HCDR2, and HCDR3 and a light chain variable region comprising complementary determining regions LCDR1, LCDR2, and LCDR3, wherein:
(a) HCDR1 comprises the amino acid sequence of SEQ ID NO: 3;
(b) HCDR2 comprises the amino acid sequence of SEQ ID NO: 4;
(c) HCDR3 comprises the amino acid sequence of SEQ ID NO: 5;
(d) LCDR1 comprises the amino acid sequence of SEQ ID NO: 6;
(e) LCDR2 comprises the amino acid sequence of SEQ ID NO: 7; and
(f) LCDR3 comprises the amino acid sequence of SEQ ID NO: 8.

2. The method of claim 1, wherein the antibody that specifically binds to the IL-6 receptor comprises a heavy chain variable region sequence of SEQ ID NO: 1 and a light chain variable region sequence of SEQ ID NO: 2.

3. The method of claim 1, wherein the subject experiences a reduction in pain indicated by a reduction of VAS to less than 40 mm after 24 weeks of treatment.

4. The method of claim 1, wherein the subject, prior to the administering the antibody, has a Disease Activity Score (DAS) of from 3.2 to 5.1.

5. The method of claim 1, wherein the subject, prior to the administering the antibody, has a DAS of greater than 5.1.

6. The method of claim 1, wherein the therapeutically effective dose for subcutaneous administration is a dose of about 150 mg or about 200 mg of the antibody at least once every two weeks.

7. The method of claim 1, wherein the inflammation control is inflammation in the subject that has been reduced by a disease-modifying antirheumatic drug (DMARD), selected from one or more of methotrexate, etanercept, infliximab, adalimumab, golimumab and certolizumab pegol.

8. The method of claim 1, wherein the subject (i) was previously ineffectively treated for rheumatoid arthritis by administering at least one DMARD different from the antibody, (ii) is intolerant of at least one DMARD different from the antibody, or (iii) is considered an inappropriate candidate for continued treatment of rheumatoid arthritis by administering at least one DMARD different from the antibody.

9. The method of claim 8, wherein the at least one DMARD different from the antibody is methotrexate or a TNF-α antagonist.

10. The method of claim 1, wherein the antibody is sarilumab.

11. The method of claim 1, wherein the subject experiences a reduction in pain indicated by a reduction of VAS to less than 40 mm after 52 weeks of treatment.

12. The method of claim 1, wherein the subject who is determined to have UP despite inflammation control is determined to have strict RP, wherein the strict RP is defined by having UP, a serum level of CRP of less than 10 mg/L and a swollen joint count (SJC) of equal to or less than 1.

13. A method for treating refractory pain (RP) in a subject in need thereof who has rheumatoid arthritis, comprising administering to a subject who is determined to have rheumatoid arthritis and RP a therapeutically effective dose of an antibody that specifically binds to an IL-6 receptor, wherein the antibody comprises a heavy chain variable region comprising complementarity determining regions HCDR1, HCDR2, and HCDR3 and a light chain variable region comprising complementary determining regions LCDR1, LCDR2, and LCDR3, wherein:
(a) HCDR1 comprises the amino acid sequence of SEQ ID NO: 3;
(b) HCDR2 comprises the amino acid sequence of SEQ ID NO: 4;
(c) HCDR3 comprises the amino acid sequence of SEQ ID NO: 5;
(d) LCDR1 comprises the amino acid sequence of SEQ ID NO: 6;
(e) LCDR2 comprises the amino acid sequence of SEQ ID NO: 7; and
(f) LCDR3 comprises the amino acid sequence of SEQ ID NO: 8
wherein the subject who is determined to have RP is characterized by having unacceptable pain (UP) and a serum level of C-reactive protein (CRP) of less than 10 mg/L, and wherein the UP has a level of pain indicated by a visual analog scale (VAS) score of greater than 40 mm.

14. The method of claim 13, wherein the antibody that specifically binds to the IL-6 receptor comprises a heavy chain variable region sequence of SEQ ID NO: 1 and a light chain variable region sequence of SEQ ID NO: 2.

15. The method of claim 13, wherein the subject who is determined to have RP further has a swollen joint count (SJC) of equal to or less than 1.

16. The method of claim 13, wherein the subject experiences a reduction in pain indicated by a reduction of VAS to less than 40 mm after 24 weeks of treatment.

17. The method of claim 13, wherein the subject, prior to the administering the antibody, has a Disease Activity Score (DAS) of from 3.2 to 5.1.

18. The method of claim 13, wherein the subject, prior to the administering the antibody, has a DAS of greater than 5.1.

19. The method of claim 13, wherein the therapeutically effective dose for subcutaneous administration is a dose of about 150 mg or about 200 mg of the antibody at least once every two weeks.

20. The method of claim 13, wherein the inflammation control is inflammation in the subject that has been reduced by a disease-modifying antirheumatic drug (DMARD), wherein the DMARD is selected from one or more of methotrexate, etanercept, infliximab, adalimumab, golimumab and certolizumab pegol.

21. The method of claim 20, wherein the subject was (1) previously ineffectively treated for rheumatoid arthritis by administering at least one DMARD different from the antibody, (ii) is considered an inappropriate candidate for continued treatment of rheumatoid arthritis by administering at least one DMARD different from the antibody, or (iii) is intolerant of at least one DMARD different from the antibody.

22. The method of claim 21, wherein the at least one DMARD different from the antibody is methotrexate or a TNF-α antagonist.

23. The method of claim 13, wherein the antibody is sarilumab.

24. The method of claim 13, wherein the subject experiences a reduction in pain indicated by a reduction of VAS to less than 40 mm after 52 weeks of treatment.

* * * * *